US006175655B1

(12) United States Patent
George, III et al.

(10) Patent No.: US 6,175,655 B1
(45) Date of Patent: Jan. 16, 2001

(54) MEDICAL IMAGING SYSTEM FOR DISPLAYING, MANIPULATING AND ANALYZING THREE-DIMENSIONAL IMAGES

(75) Inventors: Frederick W. George, III, San Marino; Wolfgang F. Kraske, Pasadena, both of CA (US)

(73) Assignee: Integrated Medical Systems, Inc., Signal Hill, CA (US)

( * ) Notice: Under 35 U.S.C. 154(b), the term of this patent shall be extended for 237 days.

(21) Appl. No.: 08/715,920

(22) Filed: Sep. 19, 1996
(Under 37 CFR 1.47)

Related U.S. Application Data
(60) Provisional application No. 60/004,126, filed on Sep. 20, 1995.

(51) Int. Cl.[7] .............................. G06K 9/42; G06K 9/56; H04N 1/393

(52) U.S. Cl. ........................ 382/257; 382/256; 382/259; 382/308; 358/451

(58) Field of Search ..................................... 382/131, 257, 382/258, 259, 102, 108, 133, 175, 256, 261, 308; 358/451

(56) References Cited

U.S. PATENT DOCUMENTS

| | | | |
|---|---|---|---|
| 4,315,309 | 2/1982 | Coli | 705/3 |
| 4,707,661 | 11/1987 | Hoenninger, III | 324/309 |
| 4,751,643 | 6/1988 | Lorensen et al. | 382/132 |

OTHER PUBLICATIONS

Kraske "Analysis and segmentation of higher dimensional data set with Fuzzy operators for representation and visualization" SPIE Engineering Press V12 pp 263–300, Mar. 1994.*

Hasegawa et al. "Automated extraction of lung cancer lesions from multislice chest CT images by using thre–dimensional image processing" Systems and Computers in Janpan vol. 25 No. 11, p. 68–77, Oct. 1994.*

Pyeron et al. "Image cellular complexes, morphological operators and skeletonization" Proceedings of SPIE vol. 2030, p. 266–275, 1993.*

Niki et al. "A 3–D display method of fuzzy shapes obtained from medical images" Systems and Computers in Japan vol. 22, No. 11, p. 72–81, 1991.*

Baets et al. "The fundamentals of Fuzzy mathematical morphology. I. Basic concepts" International; Journal of General systems vol. 23, No. 2, p. 155–71, 1994.*

Preteux et al. "On the topographical distance function" Theory and Applications of Image Analysis p. 79–86, 1992.*

Suzuki et al. "Attempt to extract 3D image of liver automatically out of abdominal MRI" Proc. SPIE vol. 1898. p. 803–808, 1993.*

(List continued on next page.)

Primary Examiner—Phuoc Tran
Assistant Examiner—Daniel G. Mariam
(74) Attorney, Agent, or Firm—Stetina Brunda Garred & Brucker

(57) ABSTRACT

A method and device for generating, displaying and manipulating three-dimensional images for medical applications is provided. The method creates a three-dimensional images from MRI or other similar medical imaging equipment. The medical imaging system allows a user to view the three-dimensional model at arbitrary angles, vary the light or color of different elements, and to remove confusing elements or to select particular organs for close viewing. Selection or removal of organs is accomplished using fuzzy connectivity methods to select the organ based on morphological parameters.

15 Claims, 23 Drawing Sheets

Microfiche Appendix Included
(6 Microfiche, 546 Pages)

U.S. PATENT DOCUMENTS

| | | | |
|---|---|---|---|
| 4,791,567 | 12/1988 | Cline et al. | 345/424 |
| 4,817,050 | 3/1989 | Komatsu et al. | 707/10 |
| 4,868,748 | 9/1989 | Crawford et al. | 382/131 |
| 4,903,202 | 2/1990 | Crawford | 382/131 |
| 4,905,148 | 2/1990 | Crawford | 382/131 |
| 4,908,148 * | 3/1990 | Crawford | 378/901 |
| 4,916,441 | 4/1990 | Gombrich | 345/169 |
| 4,945,478 | 7/1990 | Merickel et al. | 382/131 |
| 4,962,539 | 10/1990 | Takeo et al. | 382/180 |
| 5,056,146 | 10/1991 | Nishide | 382/131 |
| 5,072,384 | 12/1991 | Doi et al. | 382/132 |
| 5,142,589 * | 8/1992 | Loughheed et al. | 382/102 |
| 5,166,876 | 11/1992 | Cline | 345/424 |
| 5,179,419 * | 1/1993 | Palmquist et al. | 382/108 |
| 5,185,809 | 2/1993 | Kennedy et al. | 382/131 |
| 5,187,658 | 2/1993 | Cline et al. | 382/128 |
| 5,268,967 | 12/1993 | Jang | 382/132 |
| 5,289,374 | 2/1994 | Doi et al. | 600/407 |
| 5,319,551 | 6/1994 | Sekiguchi et al. | 382/131 |
| 5,325,293 | 6/1994 | Dorne | 705/2 |
| 5,325,449 * | 6/1994 | Burt et al. | 382/240 |
| 5,361,763 | 11/1994 | Kao et al. | 600/410 |
| 5,390,258 | 2/1995 | Levin | 382/131 |
| 5,412,563 | 5/1995 | Cline et al. | 345/420 |

OTHER PUBLICATIONS

Niki et al. "Three dimensinal imaging of blood vessels using cone beam CT" Proceedings ICIP–94 vol. 2, p. 140–14, Nov. 1994.*

Niki et al. "3D visualization of fuzzy shapes using multi-channel MR images" 1993 IEEE Conference on Nuclear Sciene Symposium and Medical imageing Conference vol. 3, p. 1647–51, Oct. 1993.*

* cited by examiner

VOXAR IMAGE REFORMATION SYSTEM
BASIC HARDWARE AND SOFTWARE COMPONENTS

VOXAR HARDWARE

1. SUN HOST 4/370GX
2. 48MBYTES MEMORY EXPANSION
3. 2 1152x960 TRINITRON MONITOR
4. CG5 COLOR BOARD
5. SUN ETHERNET INTERFACE
6. 669 MBYTE SCSI HARD DISK

VOXAR SOFTWARE

1. PIXAR CHAP VOLUMES
2. PIXAR PIRL,CHAD,CHAP
3. SUN UNIFY DATABASE
4. SUNVIEW WINDOWS
5. AT&T UNIX OPER. SYS.
6. BERKELEY SOCKETS
7. AT&T TELENET NETWORK
8. AT&T UNIX C COMPILER
9. PIXAR CHAP ASSEMBLER

PIXAR/SUN/BARCO/MATRIX/AT&T/BERKELEY

FIG. 2A

VOXAR 3D VISUALIZATION PANEL

ALPHA: 80%
300c

OPAQUE    TRANSPARENT

302c
COLOR TABLE MENU:

ANGULAR TABLE MENU
304c

INITIAL ANGLE:   0 DEG
FINAL ANGLE:    180 DEG
                                        −180            180
VIEW INCREMENT: −20 DEG

ALGORITHM MENU:
306c    VOLUME    SURFACE    GRADIENT    FUSED
        308c       310c        312c       316c

GRADIENT TABLE MENU:
SHADE DIRECTION:
LEFT−RIGHT   .8
ANT−POST     .4
SUP−INF     −.8      −1.                    1.
                                        314c

FIG. 6

RADIATION THERAPY
DYNAMIC BEAM PLANNING

DYNAMIC BEAM PLANNING MODE

PLANE SELECTION:

TRANSVERSE    |SAGITTAL|    CORONAL    OBLIQUE

INITIAL ANGLE:    −40 DEG    
       375c                   −180          180

376c
FINAL ANGLE:    60 DEG    
                          −180          180

( SHAPE )    ( CALCULATE )    ( QUIT )

RADIATION THERAPY PLANNING
BEAM SHAPING SUBMODE

377c BEAM SHAPING SUBMODE

SHAPE:    RECTANGLE    CIRCLE    |BLOCK|
WEDGE ANGLE: 379c
|NONE|    20 DEG    30 DEG    45 DEG

381c
BEAM WEIGHT:    33%    
                         0            100

( SET )

IMAGE FORM

| STRUCTURING ELEMENT FORM | | POINT | CURVE | SURFACE | VOLUME |
|---|---|---|---|---|---|
| | POINT | POINT | CURVE | SURFACE | VOLUME |
| | SEGMENT | NULL | CURVE | SURFACE | VOLUME |
| | DISK | NULL | NULL | SURFACE | VOLUME |
| | SPHERE | NULL | NULL | NULL | VOLUME |

MEDICAL IMAGING SYSTEM FOR DISPLAYING, MANIPULATING AND ANALYZING THREE-DIMENSIONAL IMAGES

This application claims the benefit of priority from U.S. Provisional Patent Application No. 60/004,126 filed on Sep. 20, 1995.

FIELD OF THE INVENTION

The present invention relates generally to medical imaging systems and digital signal processing. It relates more particularly to a method of inputting medical data into a computer, allowing the end user to efficiently visualize and manipulate the data, and processing the data according to the user instructions. The processing of the data includes the use of data-dimensional sieving and fuzzy connectivity to facilitate analysis and review of three-dimensional medical images such as those produced by magnetic resonance imaging (MRI) devices and the like.

MICROFICHE APPENDIX

A microfiche appendix containing computer source code is attached. The microfiche appendix comprises six (6) sheets of microfiche having 546 frames, including one title frame.

The program contained in the microfiche appendix can be utilized in the practice of the present invention upon Unix equipment and Pixar computers. FIGS. 2A–2C illustrate the basic hardware and software components necessary to execute the program.

The microfiche appendix contains material which is subject to copyright protection. The copyright owner has no objection to the reproduction of such material, as it appears in the files of the Patent and Trademark Office, but otherwise reserves all copyright rights whatsoever.

BACKGROUND OF THE INVENTION

Various methods exist for viewing and manipulating data to create a three-dimensional image. As those skilled in the art will appreciate, such three-dimensional images provide a valuable tool to the medical professional in a manner which is non-invasive, and which is therefore considered to be of very low risk to the patient.

Tomographic imaging techniques for use in medical applications are well known. Examples of such techniques include magnetic resonance imaging (MRI), computer aided tomography (CAT), and positron emission tomography (PET). In each of these techniques, a multi-dimensional array of volume information or a plurality of cross-sectional, two-dimensional images, i.e., slices, of a body portion are generated and processed so as to provide a three-dimensional model of the imaged body portion.

Although such three-dimensional imaging techniques have proven extremely useful for their intended purposes, they still possess inherent deficiencies which detract from their overall effectiveness. Current methods attempt to project the generated three-dimensional image directly onto a screen and thus do not allow the end user to view the three-dimensional figure from arbitrary angles or manipulate the transparency of various objects to allow underlying objects to be easily viewed. In addition, current systems do not allow the end user to easily manipulate the images.

Another problem with current methods is that it is frequently difficult to interpret the viewed two-dimensional slices or images when the anatomical structures of interest are surrounded by and/or intermixed with various other anatomical structures. The undesirable presence of such superfluous imagery only complicates the image, making it much more difficult to view and interpret the desired imagery.

For example, viewing the delicate portions of the vascular system is typically difficult since veins, arteries, and capillaries are intermixed with surrounding tissue. This makes it very difficult to distinguish the desired portions of the vascular system from surrounding tissue. Often, only slight changes in the intensity of the image distinguish a desired anatomical structure from surrounding tissue.

SUMMARY OF THE INVENTION

It is thus desirable to provide a method for isolating anatomical structures of interest such that surrounding tissue is not displayed along therewith. In this manner, the medical professional may view only the unobstructed anatomical structures of interest. This vastly reduces the complexity of the image and thus minimizes confusion as to precisely what portions of the image relate to the anatomical structure of interest.

Once the isolation has been achieved, it is also desirable to have an imaging system which allows an end user to easily manipulate objects by morphology and rearrange objects.

The embodiment of the present invention described in this application relates generally to a system for displaying, manipulating and analyzing three-dimensional medical images. However, the imaging system may also be used in many other fields, such as geological studies, entertainment, and aerospace. For example, the same technology which enables the imaging of organs within the body and morphologically removing organs for expanded observation would be useful in examining objects within the earth in search of oil or mineral deposits. The same technology could also be used for special effects in the entertainment industry. In this disclosure, the present invention is described primarily in connection with medical applications.

The current invention relates to a method of inputting a multi-dimensional array of volume data, or of inputting a series of two-dimensional medical images into a computer such that the end user can easily visualize the images in three dimensions and manipulate those images. The images, or portions of the image, can then be removed morphologically for application of diagnostic and therapeutic techniques.

Prior methods of data separation in the field of medical imaging used an amalgamation of algorithms. The present invention provides a consistent method of manipulating images using grayscale morphology and related fuzzy inreasoning. The invention uses grayscale and a structuring element size and shape to define fuzzy connectivity in the image in three dimensions. Thus, therapeutic and diagnostic applications can be accomplished, and new visualization and analysis capabilities such as extracting an image of the brain from surrounding elements are provided.

The data is input into the computer from a variety of sources. These sources include MRI, scanners, and digitized film samples. The data may be transferred to the computer using communications hookups that rely on standard transport carrier protocols, including an internet protocol. The transfer of the images over standard lines allows for remote users to access the data and greatly facilitates teleconferencing and information transfer.

The medical imaging system of the present invention generates a three-dimensional model of a body portion from either a multi-dimensional array of volume data or from a series of slices or images taken along particular planes of interest. These slices, or two-dimensional images, may be the result of MRI scans, PET scans or other medical imaging technology.

An end user chooses to view various cross-sections of the image from different angles of the three-dimensional model. The angle at which the end user views a cross-section does not necessarily correspond to the angle used to take the original image slices that are used to compose the three-dimensional model. Thus, the medical professional may review images taken along any desired plane within the three-dimensional model.

The present invention allows the medical professional to simulate treatment or provide "radiation therapy" on the three-dimensional images. The end user may choose to view the three-dimensional image under different light sources, or even expose portions of the three-dimensional model to beams of computer simulated radiation. The ability to simulate exposure to radiation and to take different views of the three-dimensional model under different lighting conditions and at arbitrary angles provides the medical specialist with a great deal of flexibility in viewing the three-dimensional image generated from a series of two-dimensional slices.

A further advantage of the invention is that it allows the end user to view only a chosen critical feature of an image. In the analysis and review of three-dimensional medical imaging, it is of critical importance to be able to measure and analyze image features having various fractal dimensionalities from zero dimensions to three dimensions. For example, veins and arteries are characterized as one-dimensional curvilinear forms, while capillaries exhibit one plus fractal dimensions, typically exhibiting fractional fractal dimensionality. Tumors have three-dimensional fractal forms and exhibit smaller fractal dimensions if metastases are considered.

The present invention specifically addresses and alleviates the above-mentioned deficiencies with the prior art. More particularly, the present invention comprises a method for isolating anatomical structures contained within a three-dimensional data set, e.g., a three-dimensional model form by MRI, a CAT scan, or a PET scan. In one embodiment, the method comprises the steps of forming a morphological skeleton of the three-dimensional data set, selecting a seed data point within the morphological skeleton so as to identify a desired anatomical structure to be displayed or analyzed, and utilizing fuzzy connectivity to define additional data points of the desired anatomical structure so as to reconstruct substantially only the desired anatomical structure. Reconstruction of substantially only the desired anatomical structure facilitates the review and analysis of the anatomical structure.

For example, if it is desirable to obtain a three-dimensional data set containing only data points which are representative of the brain, then the patient's head may be imaged via MRI, CAT, PET scanning techniques or the like to provide a three-dimensional model of substantially the entire head. The three-dimensional data set which defines this model is then processed so as to form a morphological skeleton thereof.

An operator then selects a seed data point within the morphological skeleton corresponding to the patient's brain. This is typically accomplished by viewing the morphological skeleton on a display such as a CRT. The morphological skeleton maintains all of the data available in the original three-dimensional data set. However, in the morphological skeleton, anatomical structures are separated from one another, based upon the fractal dimensionality thereof. Thus, anatomical structures having a fractal dimensionality of less than one dimension are separated from those having a fractal dimensionality of less than two dimensions and the anatomical structures are separated from those having a fractal dimensionality of less than three dimensions.

After selecting a seed data point within the brain, fuzzy connectivity is utilized to define the additional data points which are required to provide a substantially complete image of the brain. Reconstruction of the brain is simply the reverse of the process utilized to form the morphological skeleton. With the use of fuzzy connectivity to define the set of points defining the brain, it appears that all of the features thereof are substantially utilized in the reconstruction process. Reconstruction of the brain without the use of fuzzy connectivity would result in the loss of substantial fine-resolution details thereof. For example, the surface texture and even, to a lesser degree, the convolutions of the brain, would tend to be degraded or smoothed.

The morphological skeleton is formed by recursive opening and erosion of the tree-dimensional data set so as to form a plurality of residuals which define the morphological skeleton. Reconstructing a desired anatomical structure from the morphological skeleton comprises performing the opposite procedure from that utilized to form the morphological skeleton. Thus, reconstruction comprises recursive dilation and closing of the morphological skeleton. As those skilled in the art are aware, each step of opening comprises an erosion followed by a dilation and each step of the closing comprises a dilation followed by an erosion.

The use of fuzzy connectivity during the reconstruction process assures that substantially all of the data points associated with the desired anatomical structure are utilized in the reconstruction process.

According to a preferred embodiment of the present invention, a convex, such as a circle, structuring element is utilized in both the formation of the morphological skeleton and the reconstruction process. However, those skilled in the art will appreciate that various other shapes of structuring elements are likewise suitable. Indeed, it has been found that various different shapes of structuring elements are particularly suited for use with various different dimensionalities or shapes of anatomical structures.

Generally, the seed data point is selected by positioning a cursor at a desired point on an image being displayed upon a monitor. Thus, the operator may simply visually identify and manually select a seed within the organ or anatomical structure of interest. However, as those skilled in the art will appreciate, various different computer algorithms may be utilized in the selection of such a seed. For example, the operator may simply initiate an algorithm which selects the largest organ within a given volume. Thus, if the operator desires to select the brain for reconstruction, the operator could merely select the largest organ within the head.

The present invention provides a method of choosing data seed points by performing a comparison with a database. Using fuzzy seed points the medical imaging system of the present invention records the relational position of organs within the human body. From the header of the database, the gantry position, the anatomical region of interest and orientation of the patient are retrieved and used to orient the database. From a generic three-dimensional human atlas the user positions a transverse, sagittal and coronal section of the scan roughly over a general position on the human atlas. The coordinates are then used to cross correlate seed points with partially reconstructed regions, and then to perform fuzzy connectivity and tissue classification from the relational fuzzy seed points of the database throughout the remaining reconstruction. Each fuzzy seed point is specified with a resolution for reconstruction and coordinates in a coordinate system related to the actual scan data by the user overlay of transverse, sagittal and coronal sections roughly on the appropriate regions of the anatomy. By scaling, translation and rotation, other coordinates of the scans are best fitted onto the atlas for designation and reconstruction of organs. Improvements for anatomical anomalies such as unusually ordered organs, i.e., right sided heart, are adjustments for post analysis and training of the method on a multitude of data sets.

The use of fuzzy connectivity to define additional data points of the desired anatomical structure comprises defining connectivity based upon the size and shape of a structuring element utilizing a fuzzy generalization of mathematically defined distances between sets of data points as a criterion. This is accomplished based upon a modified Hausdorff metric. Thus, separation of such anatomical features from one another according to the present invention is accomplished via dimensional sieving.

Dimensional sieving results in the formation of a morphological skeleton utilizing the recursive opening and erosion processing according to well known principles. The opening and erosion processes are described in detail in "Morphological Systems for Multi-Dimensional Signal Processing" by Petros Maragos and Ronald W. Schafer, *Proceeds of the IEEE,* Volume 78, No. 4, April 1990; "Morphological Filters-Part I: Their Set-Theoretic Analysis and Relation to Linear Shift-Invariant Filters," by Petros Maragos and Ronald W. Schafer, *IEEE Transactions on Acoustics, Speech and Signal Processing,* Volume ASSP-36, No. 8, August 1987; and "Morphological Filters, Part II: Their Relations to Median Order-Statistic, and Stack Filters," by Petros Maragos and Ronald W. Schafer, *IEEE Transactions on Acoustics, Speech, and Signal Processing,* Volume ASSP-35, No. 8, August 1987.

According to the present invention, a cascade of data dimensional sieving filters are used directly with a three-dimensional image from an MI device or the like to isolate structures such as arteries and veins from surrounding tissue for unobstructed visualization. This cascade of data dimensional sieving filters comprises the use of a generally spherical structuring element, followed by the use of a two-dimensional surface structuring element, followed by the use of a curvilinear structuring element, followed by the use of a point structuring element.

Thus, to provide for the identification of desired dimensional features within the multi-dimensional data set provided by a tomographic imaging device, a data dimensional sieving algorithm separates the data based upon the dimensional characteristics of the anatomical structures contained therein. The algorithm utilizes filters which resemble geometric constructions such as lines, disks, and spheres, to sieve multi-dimensional features of curves, surfaces, and regions, as well as features of fractal dimensions in between.

A hierarchy of dimensional filters is thus utilized to first remove features of less than one fractal dimension, then to remove features of less than two fractal dimensions, and finally to remove features of less than three fractal dimensions from the original three-dimensional data set as the morphological skeleton is being formed. Thus, the cascade of filters is used directly with a tomographic image to isolate anatomical structures from surrounding tissues to facilitate analysis and review thereof.

By utilizing the residuals of morphological erosion and opening, the morphological skeleton is formed. This process is ideal for processing data with fractal dimensional components. Once the morphological skeleton has been formed via recursive development utilizing alternating opening and erosion processes, fuzzy connectivity is utilized in the reconstruction of those anatomical structures of interest. Reconstruction of anatomical structures without utilizing fuzzy connectivity results in the loss of significant features such as surface textures and roughness. Thus, these features must be reconstructed from the residuals defining the morphological skeleton utilizing fuzzy connectivity. The reconstruction of such anatomical features requires the satisfaction of a fuzzy connectivity criteria such that only those features connected to the dimensional features isolated by the sieving process are utilized.

The final result of both the sieving and fuzzy connectivity processes is a classification and clear visualization of the anatomical structures of interest, e.g., tissues and/or tumor pathologies. Additionally, quantification of the volume of organs and tumors as well as other measurements of interest, such as the diameter of arteries and veins, are easily facilitated as a direct result of the use of dimensional sieving and fuzzy connectivity.

Connectivity is a mathematical concept which states that a set of points is connected if and only if every pair of points in the set can be connected by a line which is contained within the set. The algorithm described in this invention generalizes this concept of connectivity to the discrete topological grids utilized by a computer to store the digital image data by utilizing fuzzy set operators. A fuzzy set is itself a generalization of a discrete set by defining a function over a set representing degrees of membership such that membership varies from zero which indicates no membership to one which indicates complete membership.

To define connectivity, this algorithm utilizes a fuzzy generalization of mathematically defined distances between sets as a connectivity criterion. This criterion establishes that if two points or two sets of points are within a specified distance of one another, then they have membership to the same set of points.

Fuzzy connectivity can be determined from a fuzzy distance. The fuzzy distance, d, between points provides a straight functional map, by the use of one of three different measures, into the fuzzy connectivity. The fuzzy connectivity can then be multiplied to the appropriate image as a weighing function.

The prior art attempted to isolate anatomical features from one another based solely upon the intensity of pixels within the three-dimensional data set. The present invention facilitates the distinguishing or isolation of anatomical features based upon such criteria such as size, shape, and intensity of the anatomical feature. Thus, more flexibility in designating those features to isolate is provided and improved accuracy of such isolation is attained.

These, as well as other advantages of the present invention, will be more apparent from the following description and drawings. It is understood that changes in the specific structure shown and described may be made within the scope of the claims without departing from the spirit of the invention.

BRIEF DESCRIPTION OF THE DRAWINGS

FIGS. 2A–2C is an illustration of the hardware and equipment for one embodiment system of the medical imaging system of the present invention.

FIG. 6 is an illustration of the three-dimensional visualization panel of the medical imaging system of FIG. 1.

DETAILED DESCRIPTION OF THE PREFERRED EMBODIMENT

Figure 1:
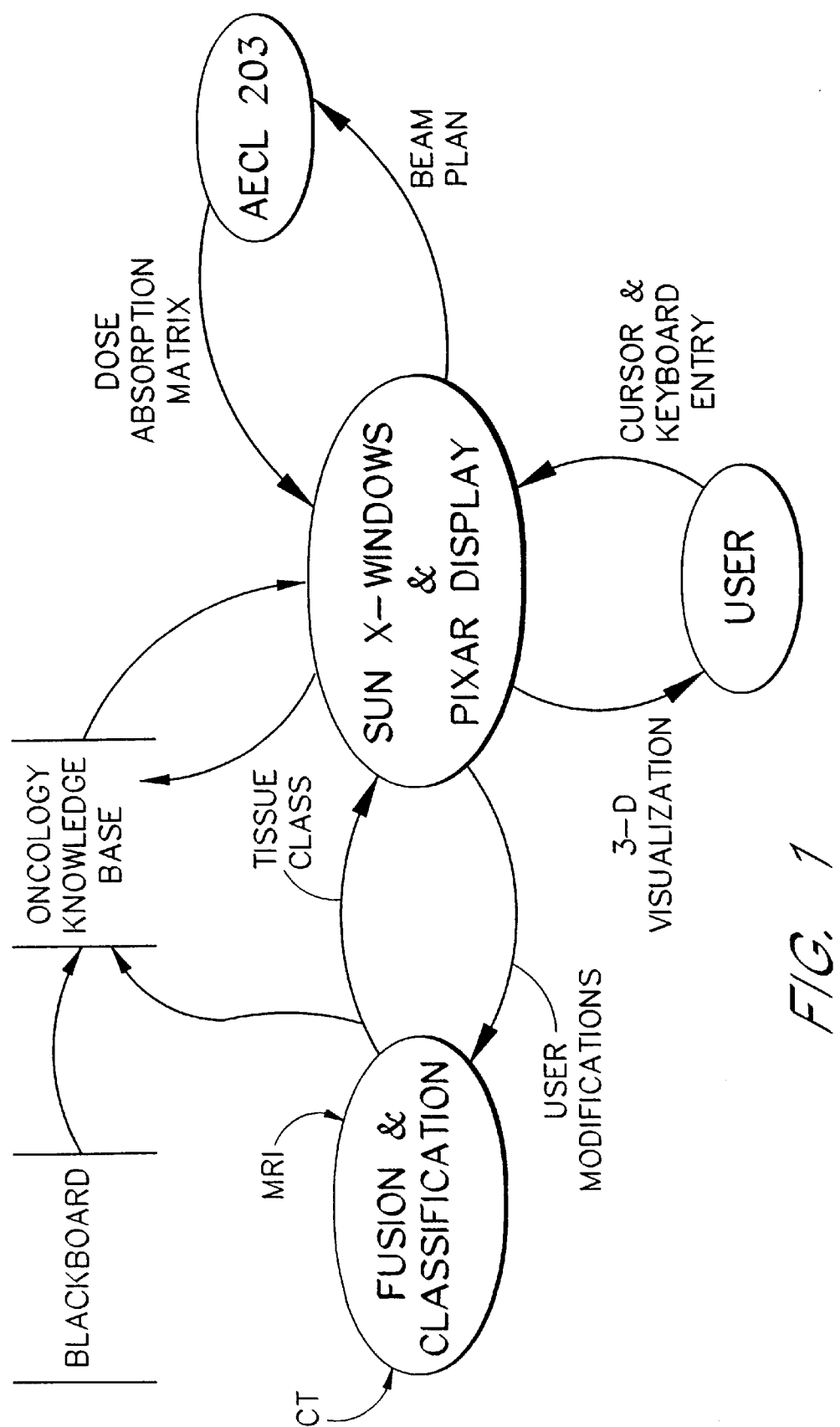
FIG. 1 is an illustration of the overall medical imaging system of a preferred embodiment of the present invention.
Figure 2B:
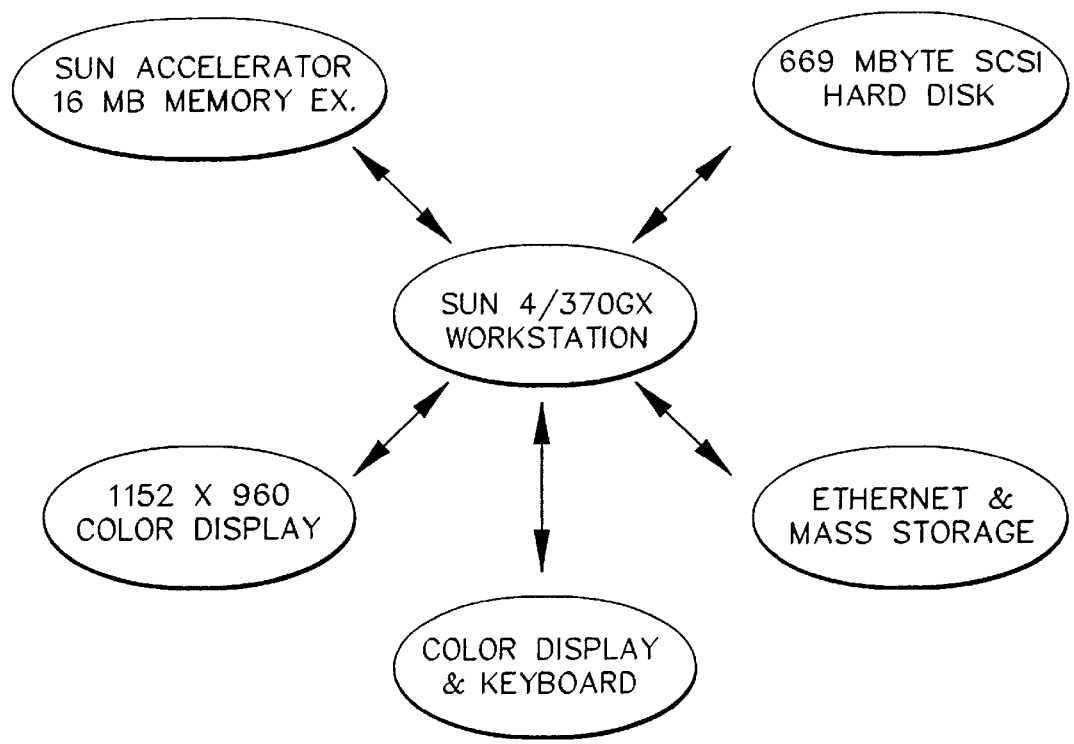
Figure 2C:
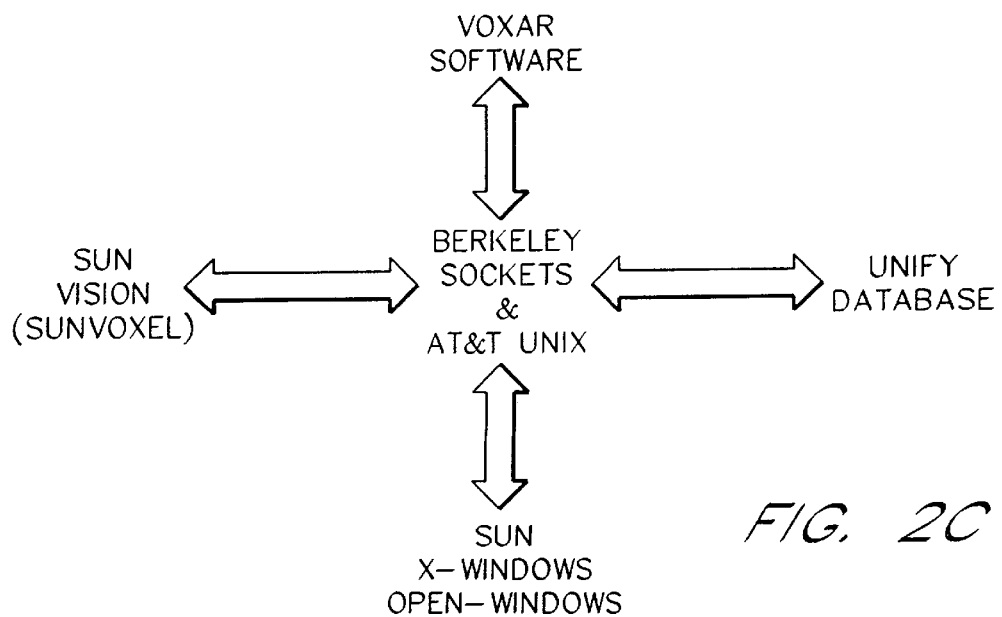

The detailed description set forth below in connection with the appended drawings is intended as a description of the presently preferred embodiment of the invention, and is not intended to represent the only forms in which the present invention may be constructed or utilized. The description sets forth the functions and the sequence of steps for constructing and operating the invention in connection with the illustrated embodiment. It is to be understood, however, that the same or equivalent functions and sequences may be accomplished by different embodiments that are also intended to be encompassed within the spirit and scope of the invention.

Provided below is a list of the symbols utilized in the math equations in this patent application:

| | |
|---|---|
| $Z^{+n}$ | Module space of integers of dimension n. |
| $Z+$ | Half space of integers greater than zero. |
| $\Re^n$ | Euclidean space of real numbers of dimension n. |
| E | Space domain of which the image is defined over, a Borel field, locally compact, Hausdorff and separable, typically a compact $\zeta^3$ or $\Re^3$ space. |
| $\Omega$ | Set of all directions from the center of the unit sphere angles of $4\pi$ steradians. |
| $\omega$ | Arbitrary angle within the range of the unit sphere $4\pi$ steradians. |
| r | A point of E of coordinates (x,y,z). |
| r | A limit point in E of coordinates (x,y,z). |
| a,d,b | Points on the real line, $\Re$, or integer domain, Z. |
| d,b | Limit point on the real line, $\Re$, or integer domain, Z. |
| d(r1,rx) | Euclidean distance between points r1 and 42. $\sqrt{(x1 - x2)^2 + (y1 - y2)^2 + (z1 - z2)^2}$ |
| B | A structuring element set, compact, convex, symmetrical to inversion, with unit radius, $.5 \cdot \|B\| = 1$. |
| \|B\| | Diameter of a set: sup $\{d(r1,r2)\|r1,r2 \in B\}$ |
| $B_r$ | A structuring element set with center translated to point r in the space E. |
| $\alpha B$ | Scale of the set B by factor $\alpha$ uniformly in all directions relative to the origin of the set coordinate system of definition. |
| X | A set in the space E or an image defined over E. |
| $X^c$ | Complement of the set X in the space E. |
| $\emptyset$ | The null or empty set. |
| $\ominus$ | Image algebraic erosion, Minkowski set subtraction. |
| $\otimes$ | Image algebraic dilation, Minkowski set addition. |

-continued

| | |
|---|---|
| $X^B$ | The closing of a set in the space E or an image defined over E with the structuring element B. $(X \circledX B) \ominus B$. |
| $X_B$ | The opening of a set in the space E or an image defined over E with the structuring element B. $(X \ominus B) \circledX B$. |
| $V(\cdot)$ | The measure defined over the space E of functional distributions mapped over the sets of E. A Lebesque measure over continuous space or the sum of voxel intensities over the integer lattice of digital imagery. |
| $\wedge$ | The infimum of the functional mappings defined over the euclidean space, for integer lattice of digital imagery this corresponds to the minimum of the functional intensity mappings of each voxel. |
| $\vee$ | The supremum of the functional mappings defined over the euclidean space for integer lattice of digital imagery this corresponds to the maximum of the functional intensity mappings of each voxel. |
| / | The set difference of binary sets in the euclidean domain or functional difference of mappings over the euclidean domain. |

In a preferred embodiment, the medical imaging system first receives data from a digital medical source such as a series of MRI images. The data is separated into two parts, a header portion and an image portion. The header portion of the data contains the dimensions of the image, patient information, scanner information, information on the facility where the images were taken and other pertinent data related to the image. This portion is converted into a system readable format and stored in a data storage section within the medical imaging system.

The image portion of the data contains the data values from the image. The image portion of the data is input into an array of voxels or pixels. The images are input first by increasing x value (across an image), then increasing y value (next row) and finally by z value (typically, z ranges from 1 to 100 in a 3-D array of voxels). Thus, the position of a voxel (x, y, z coordinates) in a particular multi-dimensional array in a scan is known by the array address.

Once the information is stored within the computer, it is capable of being processed. A series of screens, shown in FIGS. 3–10 show the user interface which allows the end user to manipulate and provide instructions to the computer. Using these controls, a user can instruct the computer to show a particular region, filter out certain elements, illuminate the three dimensional image in a particular way or expose the image to a hypothetical dose of radiation.

Figure 3A:
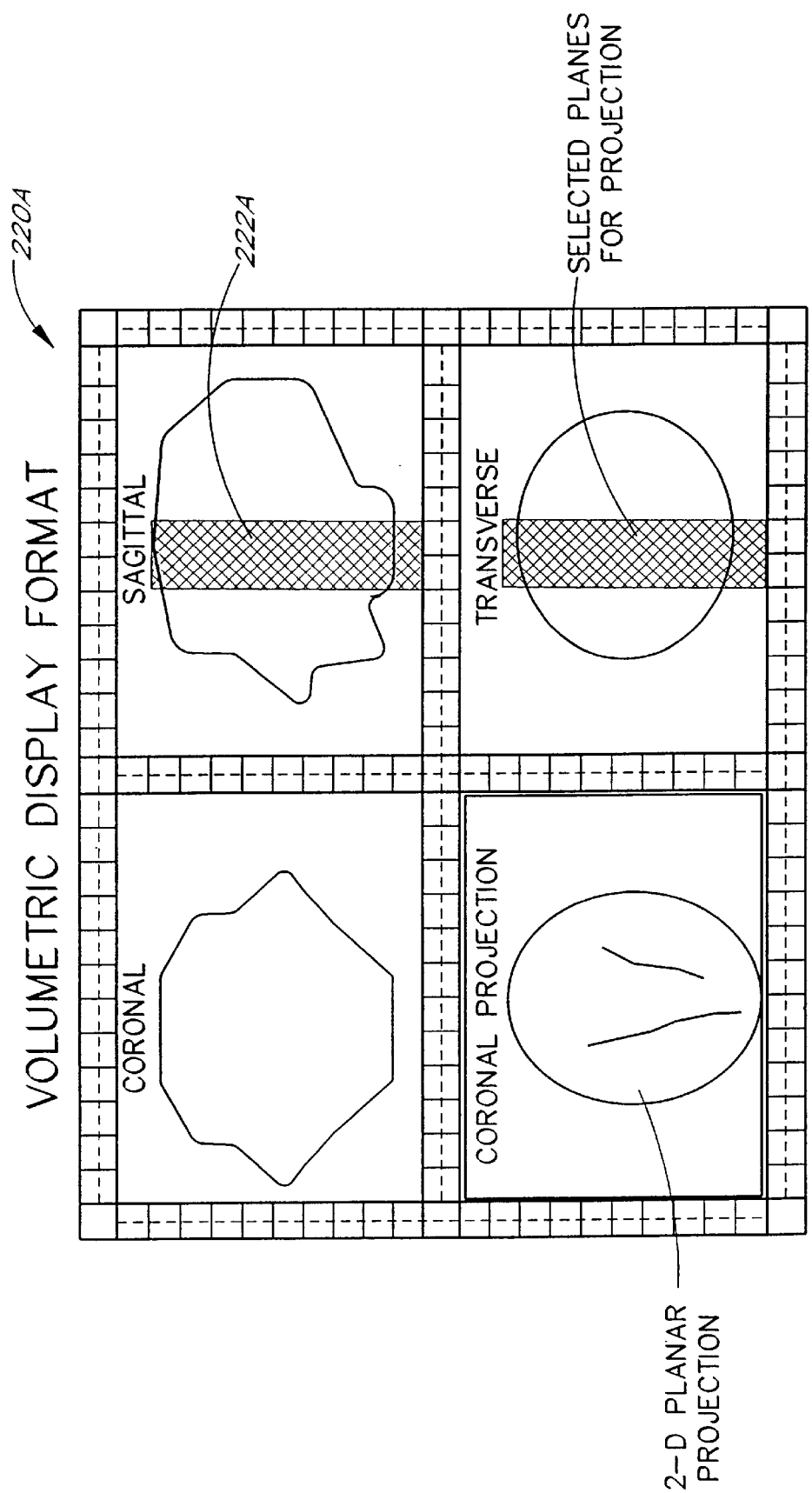
FIG. 3A is an illustration of a user screen presenting to the user options in the volumetric display format of one embodiment of the present invention.
Figure 3C:
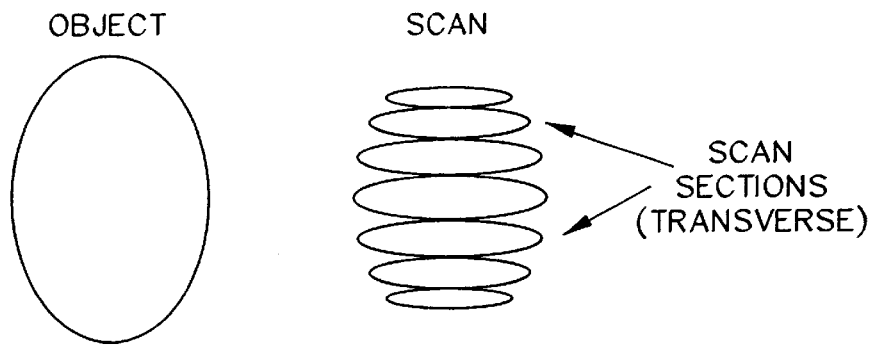
FIG. 3C is an illustration of an object and its transverse cross-sections as selected in FIG. 3A.
Figure 3B:
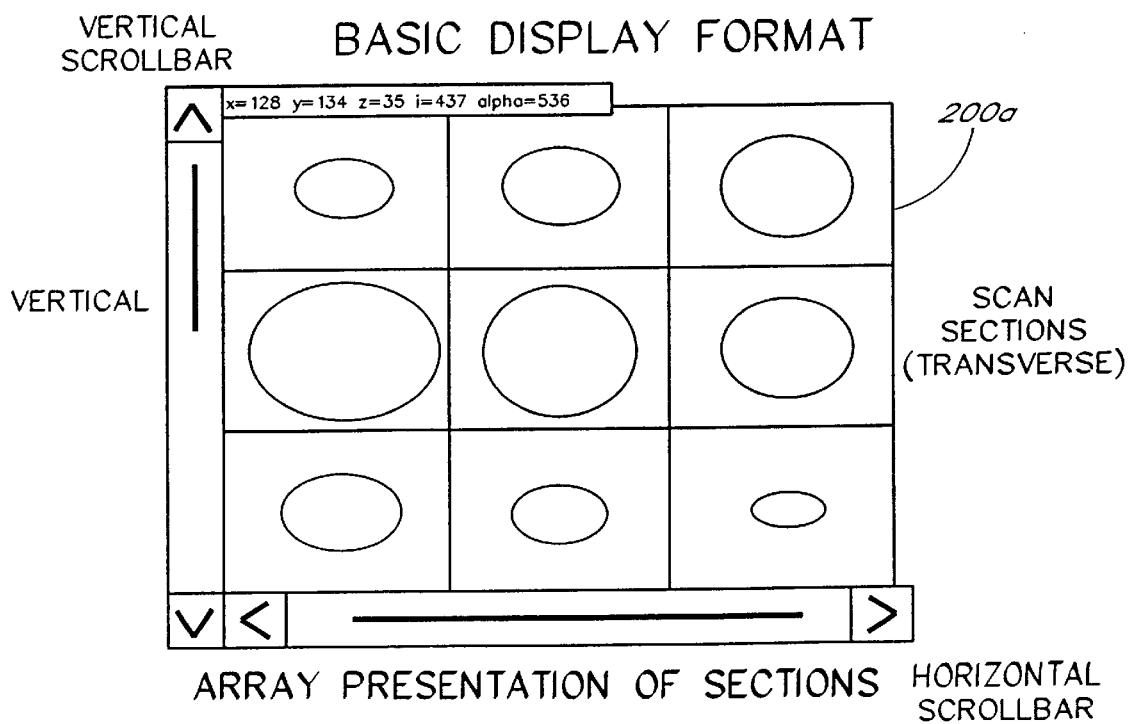
FIG. 3B is an illustration of the basic transverse display format as selected in FIG. 3A.

FIG. 3A–3C shows the display formats given to a user to choose the display. If a user merely wants to view a cross-sectional area, the user may choose from the basic display format screen 200. The user may select to view a coronal, sagittal or transverse cross-sectional area. If a three-dimensional volume is to be viewed, an appropriate volume is chosen from the volumetric display format 220.

Once a view is chosen on the volumetric display format, the user can choose the particular region or depth to be displayed by selecting a shaded region 222. The boundaries of the shaded region show the limits of what will be displayed in the three-dimensional reconstruction.

The user may also choose a particular organ or region to be displayed. The user does this by placing the cursor over an element or region to be chosen. By adjusting the size of the cursor and the position of the cursor, the user controls the pixels underneath the cursor. Once an appropriate set of pixels, generally the organ to be displayed, is set by the user, the user may click on the mouse or give some other indication that the appropriate pixels have been selected. The corresponding voxels to the pixels under the cursor will be used as the seed voxels in the morphological reconstruction of the chosen organ.

Figure 4:
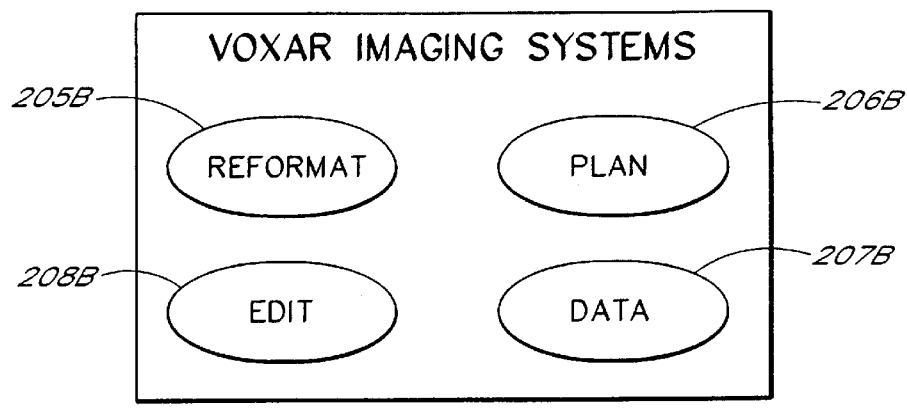
FIG. 4 is an illustration of the main menu of the medical imaging system of FIG. 1.

The main menu of the imaging system is shown in FIG. 4. The menu has four selections. Reformat 205B allows the user to choose three-dimensional axionometric projections and two-dimensional Planar interpolation functions for the volume data. The "Plan" button 206B allows the user to choose various three-dimensional radiation planning functions and decision support. The "Edit" function 208B allows for two-dimensional manual editing and three-dimensional automatic morphological editing. Within the "Edit" function are the various beam shaping algorithms and morphological tools. The "Data" function 207B includes the functions for data image input, output, manipulation and management.

Figure 5:
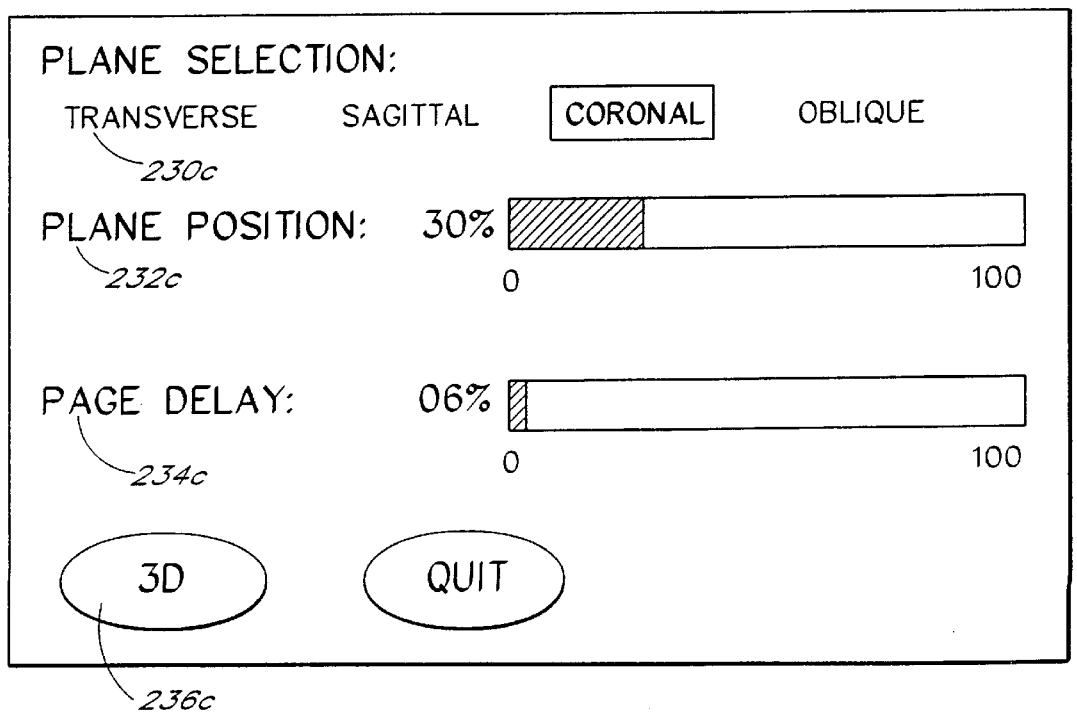
FIG. 5 is an illustration of the two-dimensional reformation panel of the medical imaging system of FIG. 1.

FIG. 5 shows the reformation panel of the imaging system 205B which appears if "Reformat" is selected. The end user can choose various planes to view by selecting the appropriate element under "plane selection" 230c. Plane position 232c permits the user to choose the position of the selected plane that will be viewed. The angle given is the position of the viewing plane relative to the normal axis of the plane selected in the "plane selection" 230c. The page delay element 234c controls the speed at which the medical imaging system will "page" or go through the two-dimensional displays. If a three-dimensional display is preferred, that selection may be made by clicking on button 236c. "Quit" exits the user from the volume two-dimensional reformation procedure.

FIG. 6 shows the display if the user elects to view the model in three dimensions. The alpha channel chosen by choosing 300c associates a second value with each pixel and provides a method of varying the level of opacity or transparency for the selected item. Thus, the user can choose to block out an item underneath the selected tissue or object by increasing the opacity or by making a particular object transparent to view what is underneath. A color table menu 302c also allows the end user to assign artificial color to various elements. The color is applied to all elements that have approximately the same gray scale morphology. An angular limits menu 304c allows the user to select the range of angles from which the object will be viewed.

An algorithm menu 306c allows the user to choose the type of three-dimensional view that will be displayed. Choosing the volume setting 308c results in a volume visualization achieved by summing voxels along rays traced through the volume element. The visualization does not include shading or artificial lights, nor does it include gradients. Thus, the image appears very similar to that presented in a x-ray or color transparency.

The surface choice 310c in the algorithm menu 308c instructs the system to review the surfaces in the data for drastic changes in intensity, for example the skull in a CT scan. The system then applies a tracing algorithm and depth shading algorithm to differentiate between surfaces.

Choosing gradient 312c results in a gradient table menu which adjusts the orientation of a light source. X-Y-Z surface gradients are generated from morphological tools as will be discussed. Gradient magnitudes are also generated. These magnitudes are compared with the inner product of artificial light sources to render the shading on various surfaces. Directional rays are used to finish the rendering of the surfaces.

The "fused" setting 316c results in combining various data distributions from different sources to create composite images. The sources combined may be two sources fused from entirely different sources or it may be combining a processed image with an unprocessed image. The algorithm for fusing data will be discussed in a later section.

Figure 7:
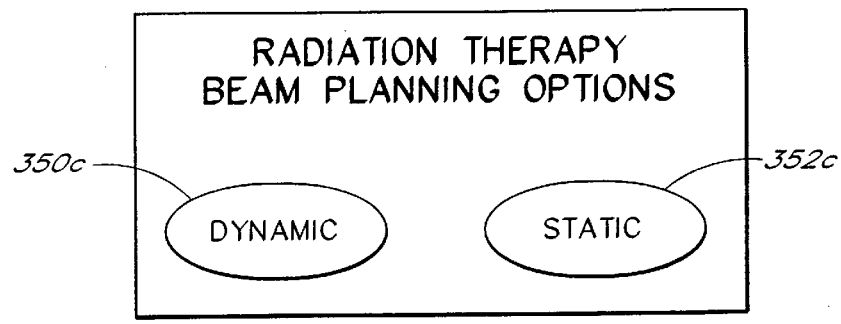
FIG. 7 is an illustration of the three-dimensional radiation therapy planning master panel of the medical imaging system of FIG. 1.

The three-dimensional image may also be manipulated, or radiation therapy applied by choosing plan from the main menu. Upon selection of plan 206B, the system provides a menu of whether dynamic or static beam planning will be conducted as shown in FIG. 7. In one embodiment, the screen view of FIG. 7 pops up upon designation of the beam planning mode to interrogate the user if a static or dynamic beam plan is desired. The dynamic selection 350c will result in iterative processing of discrete points and compensates for possible practical changes such as slight patient movement. The static selection 352c results in a calculation associated with one point in time is quicker because it requires less processing.

Figure 8:
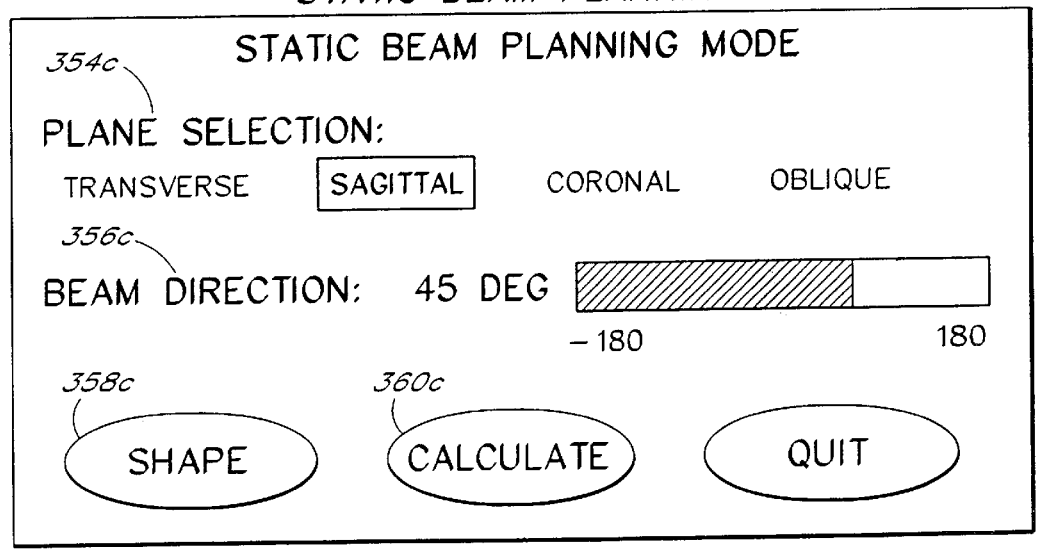
FIG. 8 is an illustration of the radiation therapy static beam planner of the medical imaging system of FIG. 1.

If a static beam plan 253c is chosen, the display shown in FIG. 8 is generated. The selection of a plan plane 354c chooses the plane that contains the static beam axis. In one embodiment, a transverse, sagittal, coronal or oblique plane may be selected. A beam direction is chosen by the control "Beam direction" 356c. The angle chosen defines the direction of the beam axis. The shape control function 358c determines the shape of the beam by calling the screen shown in FIG. 10. "Calculate" 360c designates algorithmic calculation of the beam.

Control of the beam shape is chosen by control 377c. The shape may be a rectangle, a circle or a block. Wedge angle controls 379c allow the end user to adjust beam attenuation in selected areas, thereby simulating lead wedges in actual radiation images. For example, the wedge angle may be zero degrees, 20 degrees, 30 degrees, or 45 degrees. Thus, if just surface views are desired, wedges may be placed underneath the surface. The control also permits shaping of beam dosimetry. The beam weight control, 381c permits scaled weighing of the beam dosimetry. In the screen view illustrated in FIG. 10, a block shape is selected with no wedge angle and beam weight is 33%. The shape menu permits selection of the beam shape category. The wedge angle control 379c permits shaping of the beam dosimetry by selection of a wedge shape. The beam weight 381c is a scale factor weighting of the beam dosimetry. By selecting "set", the beam shape parameters are fixed.

Referring back to FIG. 8, after the beam parameters have been defined, the "calculate" control 360c initiates algorithm calculation of the beam. The calculation may involve superimposition of the beam pattern on a three-dimensional image. As the position of the slices change, accurate computer modeling of the radiation distribution across the pixels in each slice is displayed. The simplest computations assume a linear attenuation of the beam. Exponential attenuations of the beam may also be achieved by multiplying the beam with an exponentially decaying scaling factor. A detailed description of the above methods of beam modeling along with other models are available from the reference Harold Alfred Johns and Robert Cunningham, *Physics of Radiology 4th Ed.*, 1983, (Charles Thomas Publisher) 1983. Kenneth R. Case & Walter R. Nelson, *Concepts of Radiation Dose Symmetry* 1978 (Pergamon Press Inc.); Faiz M. Khan, *The Physics of Radiation Therapy* 1984 (Walliams and Wilkins).

Figure 9:
FIG. 9 is an illustration of the radiation therapy dynamic beam planner.
Figure 9:
Figure 10:
FIG. 10 is an illustration of the radiation therapy planning beam shaping submode screen of the medical imaging system of FIG. 1.

If the dynamic beam plan 350c of FIG. 7 is selected, the display shown in FIG. 9 is generated. The dynamic planning screen shown in FIG. 9 is generally similar to the static beam planning screen of FIG. 8. Dynamic beam planning is distinguished from static beam planning by the required designation of the beam initial and final beam axis within the selected beam rotation plane. A transverse sagittal, coronal or oblique plane may be selected. In addition, initial and final beam axis controls 375c and 376c are available. These controls enable the end user to vary the beam through a variety of angles in the plan plane. For example, as illustrated in FIG. 9, an initial angle of 40 degrees and a final angle of 60 degrees are specified.

The data-dimensional sieving and connectivity methodology utilized in the present invention is illustrated in FIGS. 11–23, which depict a presently preferred embodiment of the invention.

Figure 11:
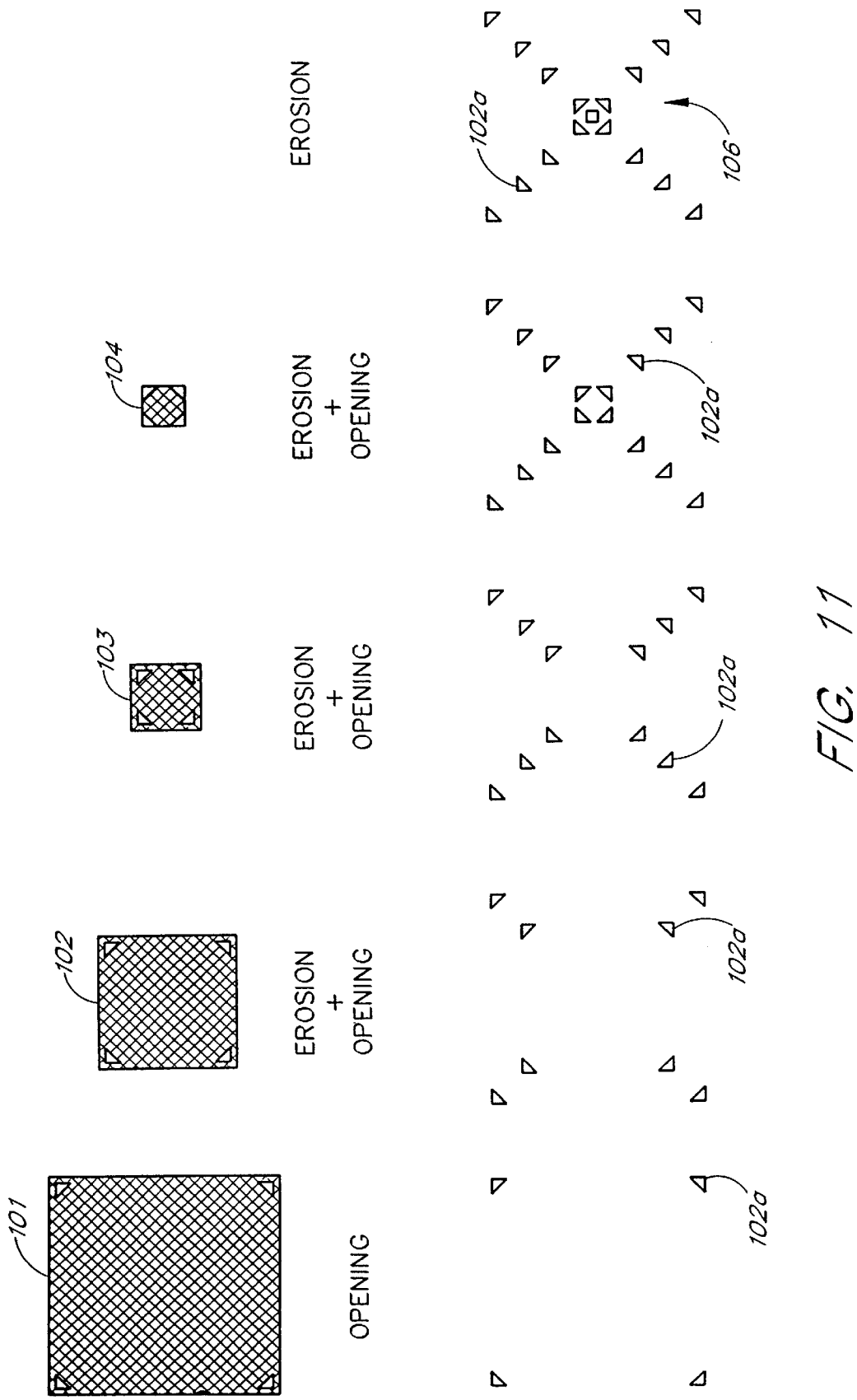
FIG. 11 is an illustration of the recursive alternating opening and erosion processes for two dimensions utilized to define the residuals of which the morphological skeleton is constructed.

Referring to FIG. 11, the recursive development of a morphological skeleton utilizing alternating opening and erosion process is shown utilizing a two-dimensional geometric construction, i.e., a square, for purposes of illustration. Although a two-dimensional example is provided herein, for purposes as illustration, those skilled in the art will appreciate that use of the present invention in medical imaging typically requires the recursive use of a three-dimensional structuring element, such as a sphere, a two-dimensional structuring element such as a surface, a one-dimensional structuring element such as a curve, and a zero-dimensional structuring element, i.e., a point.

Figures 12, 13:
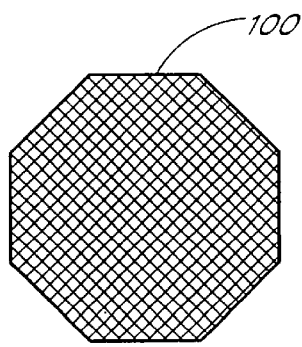
FIG. 12 shows the two-dimensional structuring element utilized in the process for forming the morphological skeleton shown in FIG. 1.
FIG. 13 is a chart giving the results of utilizing structuring elements of different forms or dimensionalities upon images of different forms or dimensionalities.

After the first opening process, a square 101 having the corners removed therefrom is defined. An octagon 100, as shown in FIG. 12, is utilized as the structural element for this example. The corners 102a are the residuals of the opening process for the original square. Each time an additional erosion and opening process is performed, progressively smaller squares 102, 103, and 104 are formed. After each recursive erosion and opening process, additional residuals 102a are defined. After the last erosion process is performed, the square is completely eliminated and the collection of residuals defines the desired morphological skeleton 106.

Dilation and erosion are defined as follows:
erosion, $$(g \oplus f_a)(x) = \min_{d \text{ in } E} \{g(x+d) - (f_a(d) - f_a(0))\} \qquad (1)$$

dilation, $$(g \oplus f_a)(x) = \max_{d \text{ in } E} \{g(x+d) - (f_a(d) - f_a(0))\} \qquad (2)$$

$$= -(-g \oplus f_a)(r)$$

Structuring element, f, and image function, g, defined over domain of definition for F,E, $$f_a(x) = af\left(\frac{x}{a}\right). \qquad (3)$$

$$d = \inf\{\alpha | \inf(Z_{\alpha g}) = \sup(X_{\alpha g}), \alpha \varepsilon \mathcal{R}+\}, \qquad (4)$$

denotes the real numbers $\geq 0$ $$S\varepsilon_\alpha(g,X) = (X \ominus \alpha g) - (X \ominus \alpha g)_{+\varepsilon g}, +0 - 1 im_{\varepsilon 10} \varepsilon$$

Alternately for a black skeleton the extensive operations of dilation and closing are performed.

$$b = \inf\{\alpha | \inf(X^{\alpha g}) = \sup(X^{\alpha g}), \alpha \in \mathcal{R}+\}, \alpha g - g(x/\alpha), \qquad (6)$$

$$S\varepsilon_{-\alpha}(g,X) = (X \oplus \alpha g) 31 \ (X \oplus \alpha g)_{+\varepsilon} g, \alpha \geq 0$$

For digital raster formats of pixels or voxels, d is limited to the integer domain Z of the data and $\varepsilon$ is equal to 1.

i.e. $S(g,X) = \Sigma_{-b \leq \alpha \leq d} S_\alpha(g,X)$, is the total skeleton.

As discussed above, opening is defined as a single erosion step followed by a single dilation step and closing is defined as a single dilation step followed by a single erosion step.

By decreasing the size of the structuring element 100, smaller residuals 102 are obtained and the resolution of the morphological skeleton is increased.

This morphological skeleton contains all of the information contained in the original image. The original image can be reconstructed from the morphological skeleton by reversing the recursive development process, i.e., by substituting dilation and closing for erosion and opening, respectively. Thus, by performing a series of dilations and closing, instead of the openings and erosions performed previously, the original three-dimensional data set is obtained from the morphological skeleton.

In forming the morphological skeleton 106, data dimensional sieving is performed such that anatomical structures having various dimensionalities are separated from one another in a manner which isolates them and makes them identifiable via computational methodology. Thus, according the methodology of the present invention, those anatomical structures having a fractal dimensionality of less than one dimension are separated from those anatomical structures having a fractal dimensionality of less than two dimensions, both of which are separated from anatomical structures having a fractal dimensionality of less than three dimensions.

A desired anatomical structure which has been so isolated and identified can then be reconstructed by reversing the recursive morphological skeleton development sequence described above utilizing only the data points associated with the selected anatomical structure. However, merely reconstructing the desired anatomical structure results in the loss of significant features such as surface textures and roughness.

Thus, in order to preserve such significant features, it is necessary to utilize fuzzy connectivity during the reconstruction process. The use of fuzzy connectivity assures that all of the data points associated with the anatomical structure are utilized in the reconstruction process. In accordance with one embodiment of the present invention, fuzzy connectivity defines the entire data set for the desired anatomical structure by utilizing a modified Hausdorff metric, wherein connectivity is defined by the size and shape of the structuring element.

For example, the structuring element is first centered upon a seed pixel by the operator. The seed pixel is one which the operator knows is a part of the anatomical structure for which reconstruction is desired. All other pixels contained within the volume defined by the structuring element are then considered to be a part of the anatomical structure being reconstructed. This process is then repeated for each new pixel within the data set until no additional new pixels are found. Although, as in the formation of the morphological skeleton, many different sizes and shapes of structuring elements are suitable, those generally spherical in configuration are preferred.

A series of different structuring elements may be utilized in either of the formation of the morphological skeleton or in the reconstruction process, as desired, so as to achieve a desired effect.

In certain embodiments of the present method, data is fused from at least a first and a second medical image, using the following initial steps: (1) reducing the second image to a size and scale corresponding to the first image; (2) converting the second image into a coordinate system corresponding to a predetermined coordinate utilized by a computer; (3) converting the first image into a coordinate system corresponding to the predetermined coordinate utilized by the computer; and (4) using different resolutions and computer distance metrics to align the first image and the second image. In addition, conversions of the second image into the predetermined coordinate system and conversion of the first image into the predetermined coordinate system can be accomplished using a series of rotations and translations.

As mentioned above, connectivity is a mathematical concept which states that a set of points is connected if and only if every pair of points in the set can be connected by a line contained in the set. The algorithm described in this invention generalizes this concept of connectivity to the discrete topological grids of computers and digital image data with fuzzy set operators. A fuzzy set is itself a generalization of a discrete set by defining a function over a set representing degrees of membership from no membership as represented by a zero to complete membership as represented by a one. This algorithm utilizes convex fuzzy membership, as shown in FIG. 17, functions defined over convex set supports.

To define connectivity, this algorithm uses a fuzzy generalization of mathematically defined distances between sets as a connectivity criterion. This criterion establishes that if two points or two sets of points are within a specified distance of one another, then they have membership to the same set of points. To more precisely define this concept of connectivity, the neighborhood of points and the data must be defined.

Figure 17:
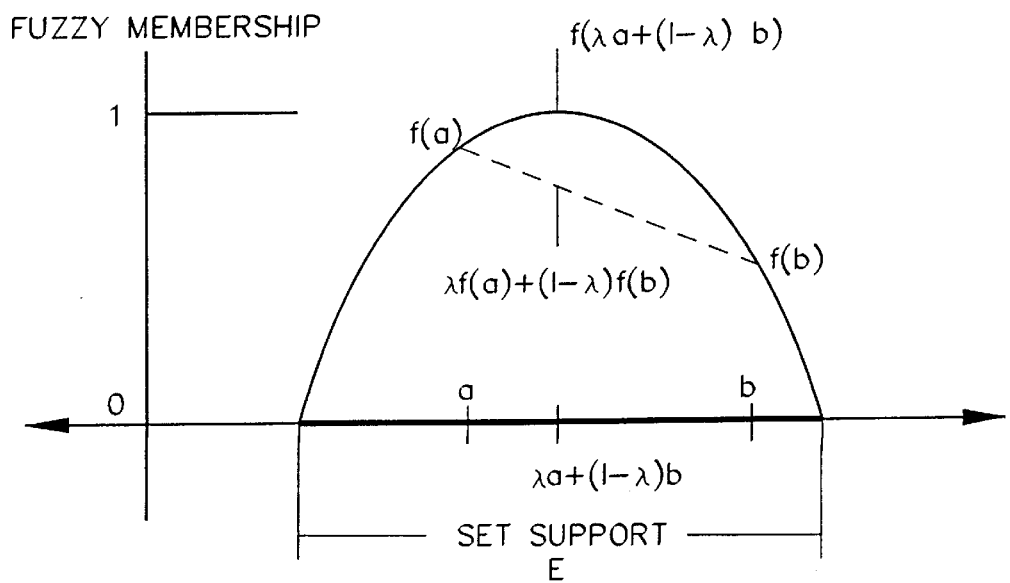
FIG. 17 shows the set support function which defines the degree of fuzzy membership for a given pair of points, which is determined by the modified Hausdorff metric for those points.

As shown in FIG. 17, convexity implies that a line fixed between any two points on the curve of the function must lie on or below the graph of the function:

$$\lambda f(a)+(1-\lambda)f(b) \leq f(\lambda a+(1-\lambda)b), \ 0 \leq \lambda \leq 1$$

erosion, $$(g \ominus f_a)(x) = \min_{d \ \text{in} \ E}[g(x+d) - (f_a(d) - f_a(0))],$$

dilation, $$(g \oplus f_a)(x) = \max_{d \ \text{in} \ E}[g(x+d) - (f_a(-d) - f_a(0))]$$

$$= -(-g \ominus f_a)(r)$$

Structuring element, f, and image function, g, defined over domain of definition for f, E, $$f_a(x) = af\left(\frac{x}{a}\right)$$

Minimum Function      Maximum Function $(g \wedge h)(x) = \min\{g(x), h(x)\}$.    $(g \vee h)(x) = \max\{g(x), h(x)\}$ Based on the previous definitions, a measure of distance between sets or points g, h can be defined. This metric is used as a membership criteria to define points or sets to be joint members using a criteria such as distance within a predefined maximum.

2.4.1 Definition: Modified Hausdorff distance metric which gives us the fuzzy distance $$d_f(g, h) = \min_{x \ \text{in} \ E}\left\{\alpha \ \text{such that} \ \min((g \wedge h)(x)) < \min_{x \ \text{in} \ E}(((((g \oplus f_a) \wedge h \oplus f_a))(x)) - ((g \wedge h)(x)))\right\}$$

than 0.

Referring back to FIG. 13, a chart showing the result of utilizing a structuring element of a particular form or dimensionality on an image of a particular form or dimensionality is shown. The chart includes structuring elements of point, segment, disk, and sphere form and images of point, curve, circles, and volume form. As shown in the chart, utilizing a structuring element defined by a point, for example, in the processing of a curve according to the methodology of the present invention, yields a curve. Similarly, utilizing a segment in the processing of a curve yields a curve and utilizing a disk or sphere in the processing of a curve provides a null product, since a two-dimensional disk or a three-dimensional sphere cannot be utilized to process a one-dimensional curve.

Figure 14:
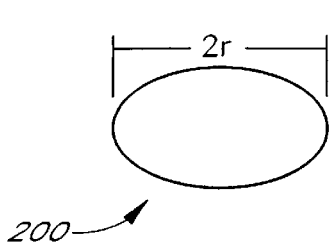
FIG. 14 shows a representative two-dimensional structuring element utilized in the fuzzy connectivity restructuring process wherein 2r is the major diameter thereof.
Figure 15:
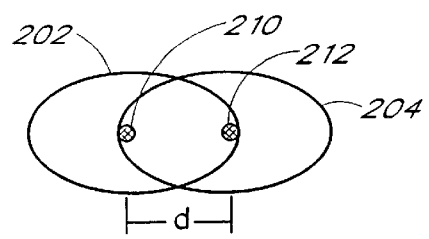
FIG. 15 shows the use of the structuring element of FIG. 4 to determine that two points belong to the same set, i.e., a set of data points defining a desired anatomical structure for reconstruction, the two points belong to the same set since when one of the points is located at the center of the structuring element, the other point falls within the bounds defined by the structuring element, wherein the dimension d defines the dimension between adjacent points such that the points fall within the set.
Figure 16:
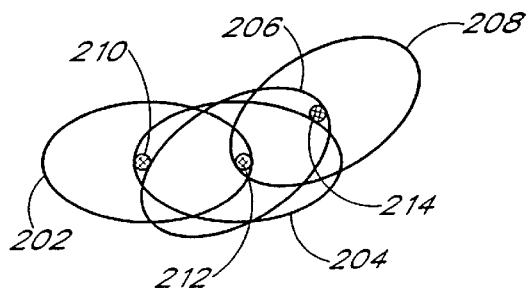
FIG. 16 shows the use of the restructuring element of FIG. 4 to iteratively determine that the set points illustrated are contained within a common set.

Referring to FIGS. 14–16, the use of a two-dimensional example of a structuring element and the fuzzy connectivity reconstruction of a desired anatomical structure is shown. With particular reference to FIG. 14, the structuring element 200 shown comprises an ellipse having a major diameter of 2r. Those skilled in the art will appreciate that various other shapes are likewise suitable for use as a structuring element.

Referring to FIG. 15, use of the structuring element to determine if two points are within a common set is shown. This is accomplished by placing the structuring element 202 around one of the points 210 of interest and then determining whether or not the second point of interest 212 lies within the boundary of the structuring element 202. As shown, the second point 212 does lie within the boundary of the first structuring element 202. In order to find additional points which are part of the common set of points, and define the anatomical structure of interest, this process is repeated by placing a structuring element 204 around the second point 212 in order to determine if any points lie within the boundary thereof.

With particular reference to FIG. 16, this process is repeated to define all of the points which belong to a common set of data points and define the anatomical structure of interest. Structuring element 202 formed about point 210 defines point 212 as being included within the data set, structuring element 204 formed about point 212 similarly defines point 210 as belonging to the common data set, while structuring element 206 formed about point 212 defines point 214 as belonging to the common data set. Thus, all points which lie within the boundary of any structuring element at which a point within the data set is formed at the center thereof, also are members of the common data set.

Each point so defined to be within the data set is assigned a fuzzy membership number between zero and one, depending upon the distance between adjacent points, as discussed above.

Thus by utilizing fuzzy connectivity, the set of all data points defining a particular anatomical structure of interest are defined such that surface details of the anatomical structure, such as surface smoothness thereof, are maintained during the reconstruction process and are thus included in the reconstructive anatomical structure.

Figure 18:
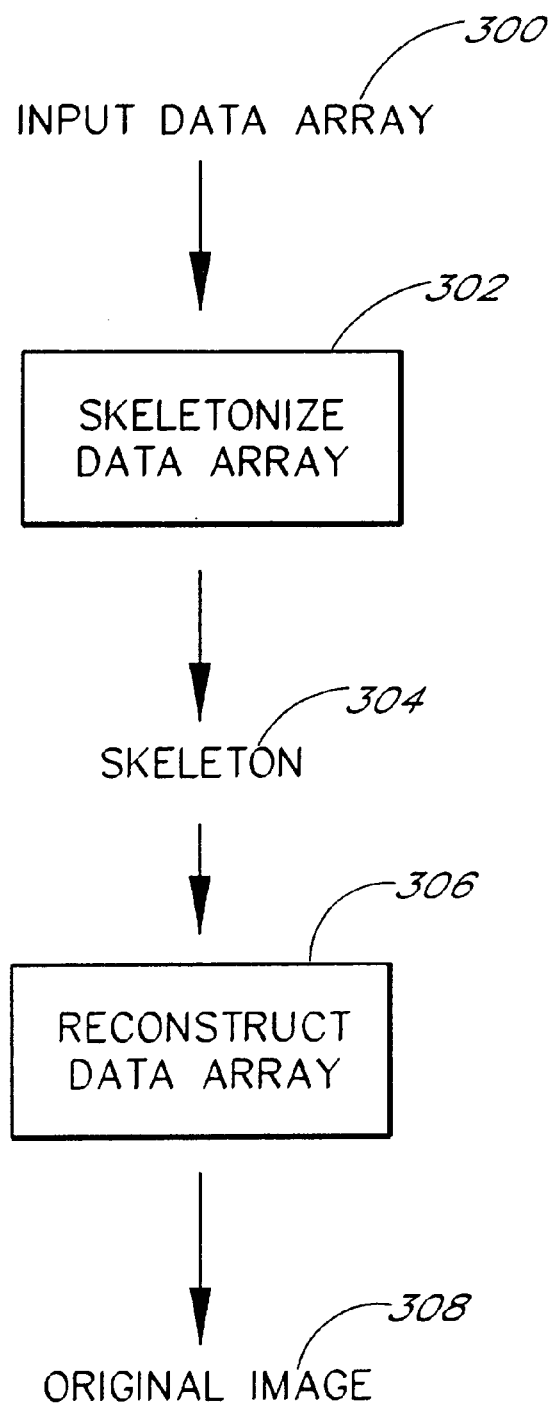
FIG. 18 is a block diagram of the conventional morphological data decomposition and reconstruction processes.

An overview of a standard morphological decomposition and reconstruction process is shown in FIG. 18. According to contemporary methodology, an input data array 300 is skeletonized 302 to form skeleton 304. Skeleton 304 is then reconstructed 306 so as to provide the original image 308. This process is used in various different data analysis, compression, and data signal processing applications.

Figure 19:
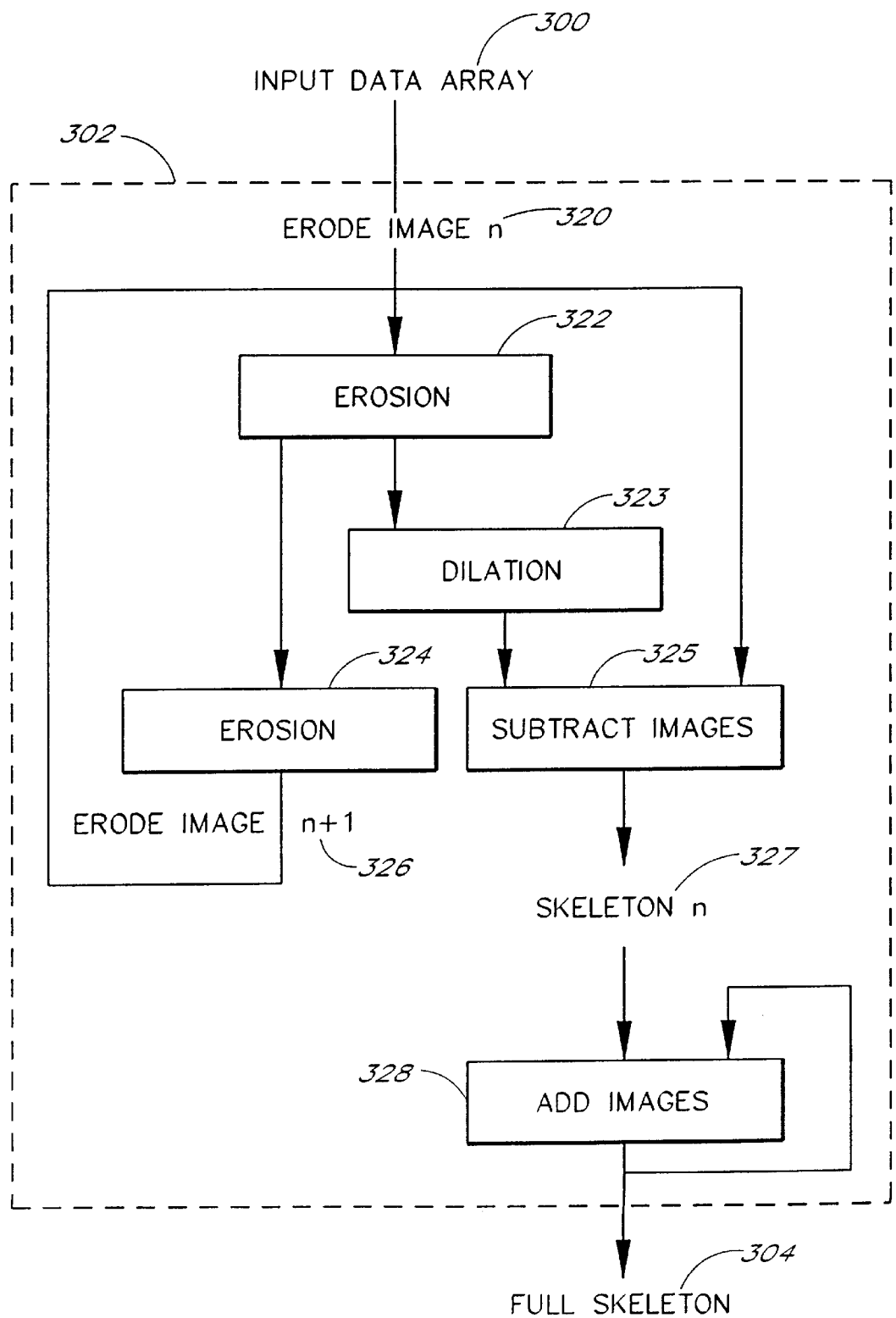
FIG. 19 is a block diagram of the morphological data skeletonization process of a preferred embodiment of the present invention.

Referring to FIG. 19, morphological data skeletonization according to the present invention is shown. Morphological data skeletonization is a recursive process wherein erode image n 320 subjected to erosion 322. The product of erosion is then subjected to dilation 323 and in parallel is subjected to erosion 324. The product of erosion 324 is erode image n+1 326 which then becomes new erode image n 320 and is iteratively processed. The product of dilation 323 is subjected to subtraction 325 with respect to erode image n 320 so as to form skeleton 327 which is then subjected to addition with full skeleton 304.

Figure 20:
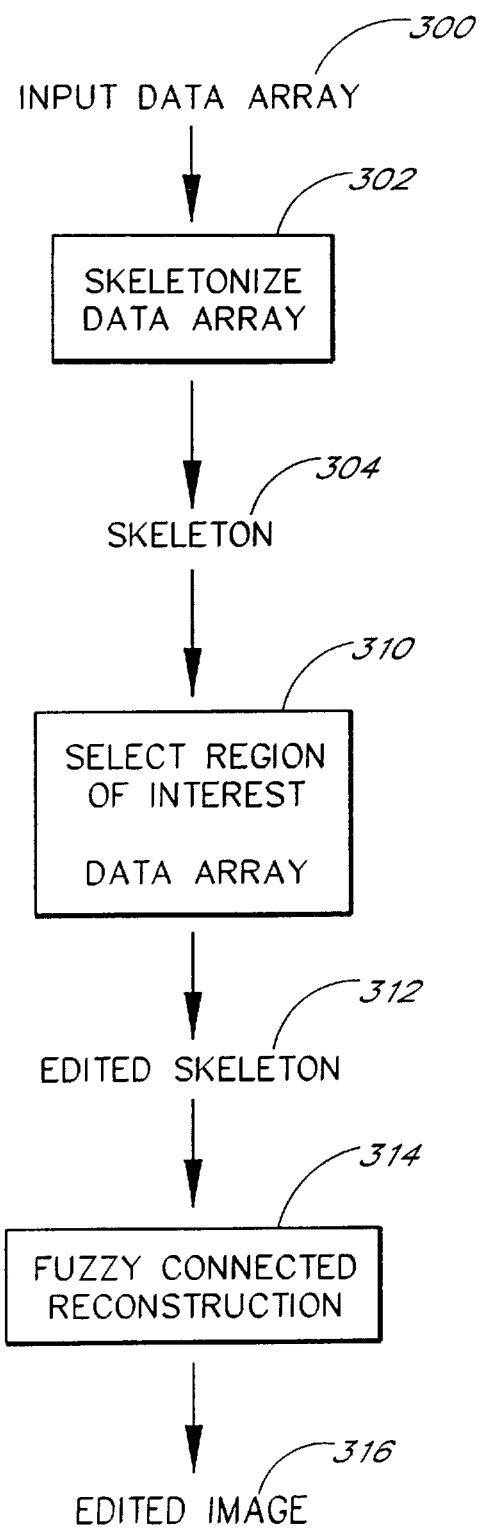
FIG. 20 is a block diagram of the morphological data decomposition and selective reconstruction processes of a preferred embodiment of the present invention.

Referring to FIG. 20, morphological data decomposition and selective reconstruction according to the present invention is shown. Input data array 300 is subjected to skeletonization to form skeleton 304. Skeleton 304 is used for the selection of a region of interest 310 so as to form edited skeleton 312. Fuzzy connectivity 314 is applied to the edited skeleton 312 to form the edited image 316.

Figure 21:
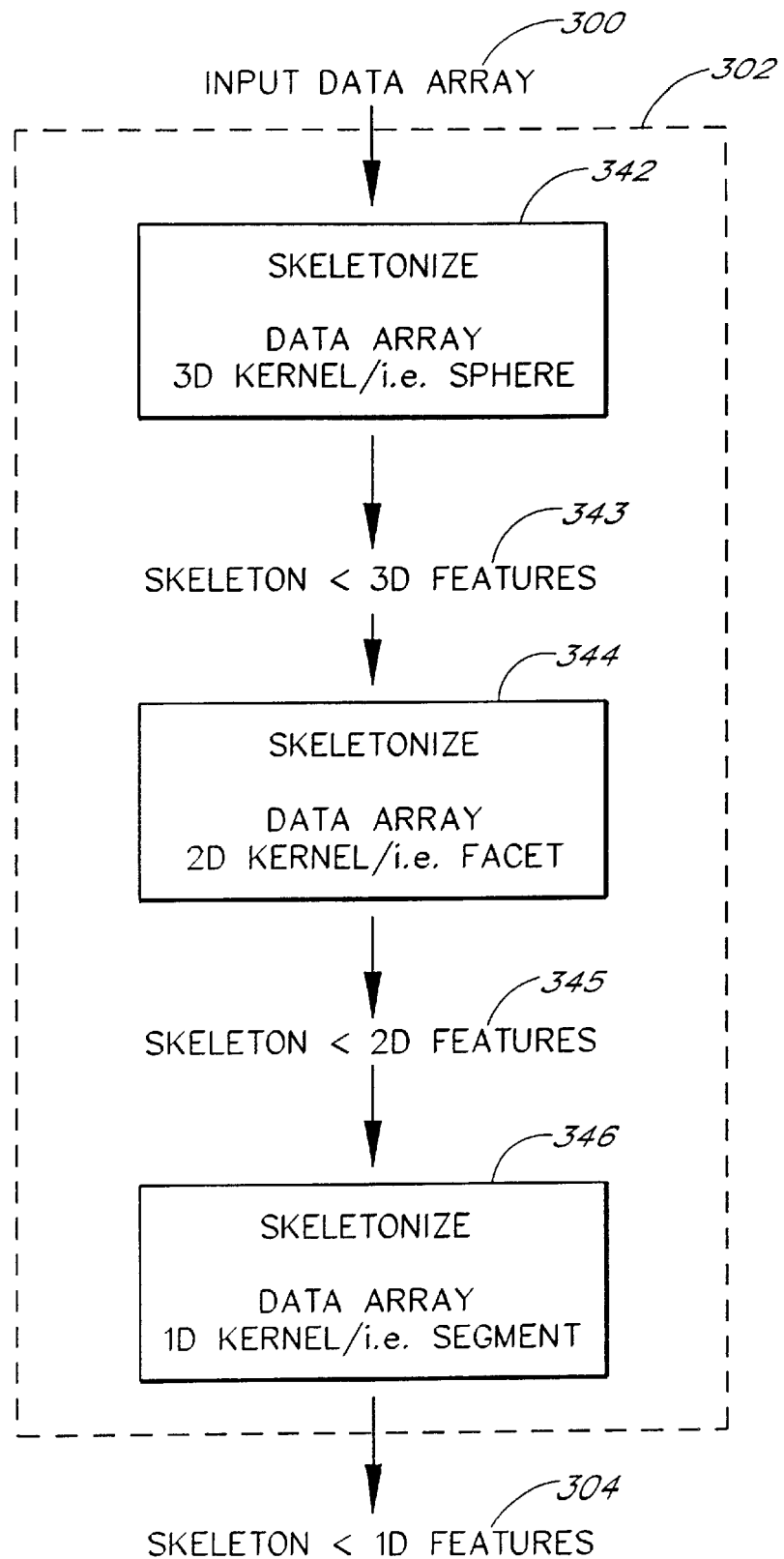
FIG. 21 is a block diagram of the morphological data dimensional sieving decomposition and selective reconstruction processes using fuzzy connectivity utilizing a three-dimensional example.

FIG. 21 illustrates, a three-dimensional example of the process of morphological data dimensional sieving, decomposition, and selective reconstruction is shown. Input data array 300 is skeletonized 342 wherein a three-dimensional kernel or structuring element configured as a sphere, for example, is utilized in the skeletonization process. The skeletonization 342 results in the formation of a skeleton 343 having less than three-dimensional features. This skeleton is then subjected to skeletonization 344 utilizing a two-dimensional kernel or structuring element configured as a facette. This two-dimensional skeletonization process 344 results in a skeleton having less than two-dimensional features 345. This skeleton having less than two-dimensional features 345 is then subjected to skeletonization utilizing a one-dimensional kernel or structuring element 346 so as to provide a skeleton having less than one-dimensional features 304.

Figure 22:
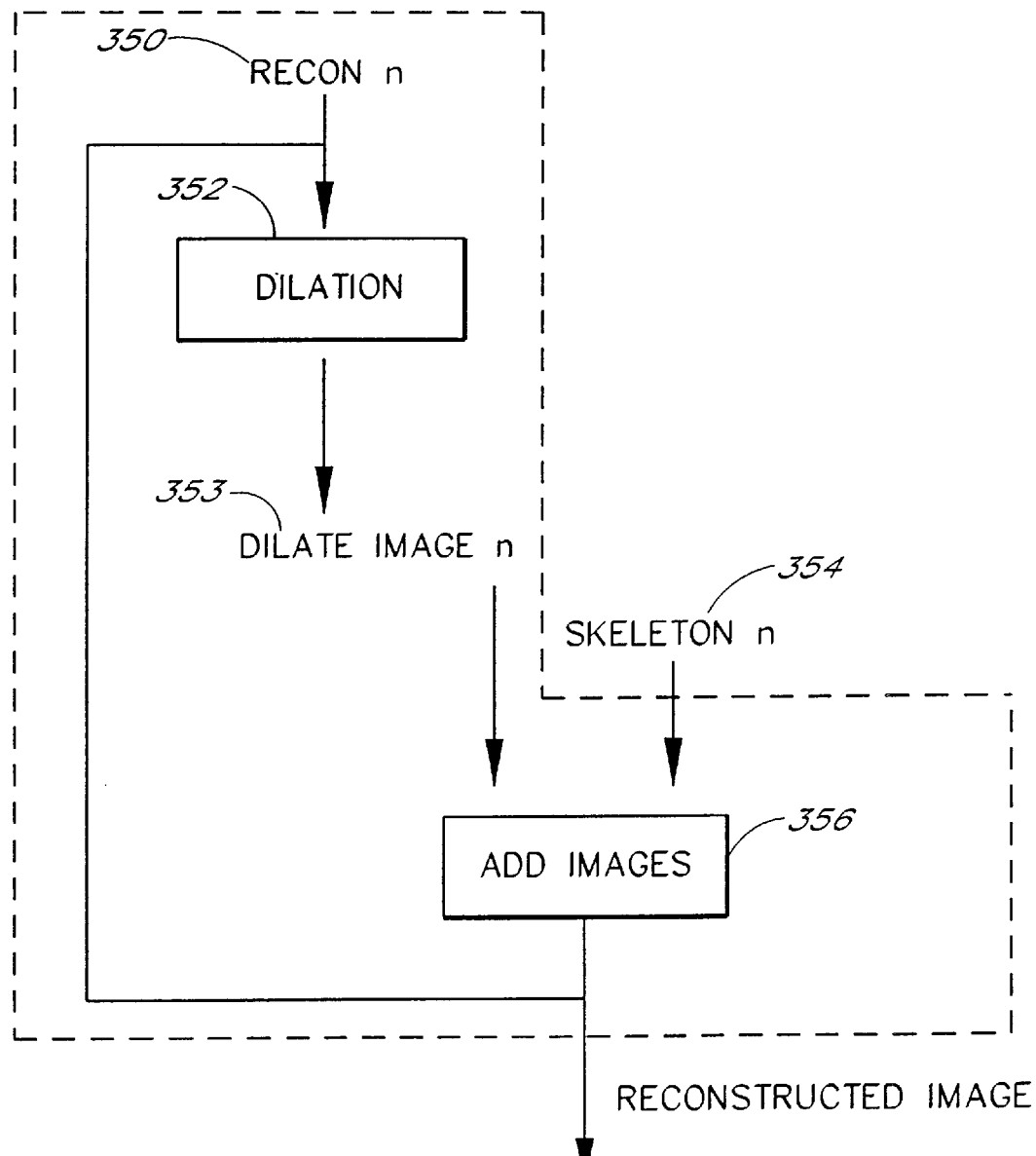
FIG. 22 is a block diagram of the morphological data reconstruction from skeleton process without using fuzzy connectivity of a preferred embodiment of the present invention.

Referring to FIG. 22, the process of morphological data reconstruction from a skeleton without the use of fuzzy connectivity is shown. As discussed above, such reconstruction results in the loss of substantial surface detail. Using reconstruction n 350, dilation 352 is performed so as to produce dilate image n 353, dilate image n 353 and skeleton n 354 are added and the process is iterated by providing the added images as reconstruction n 350.

Figure 23:
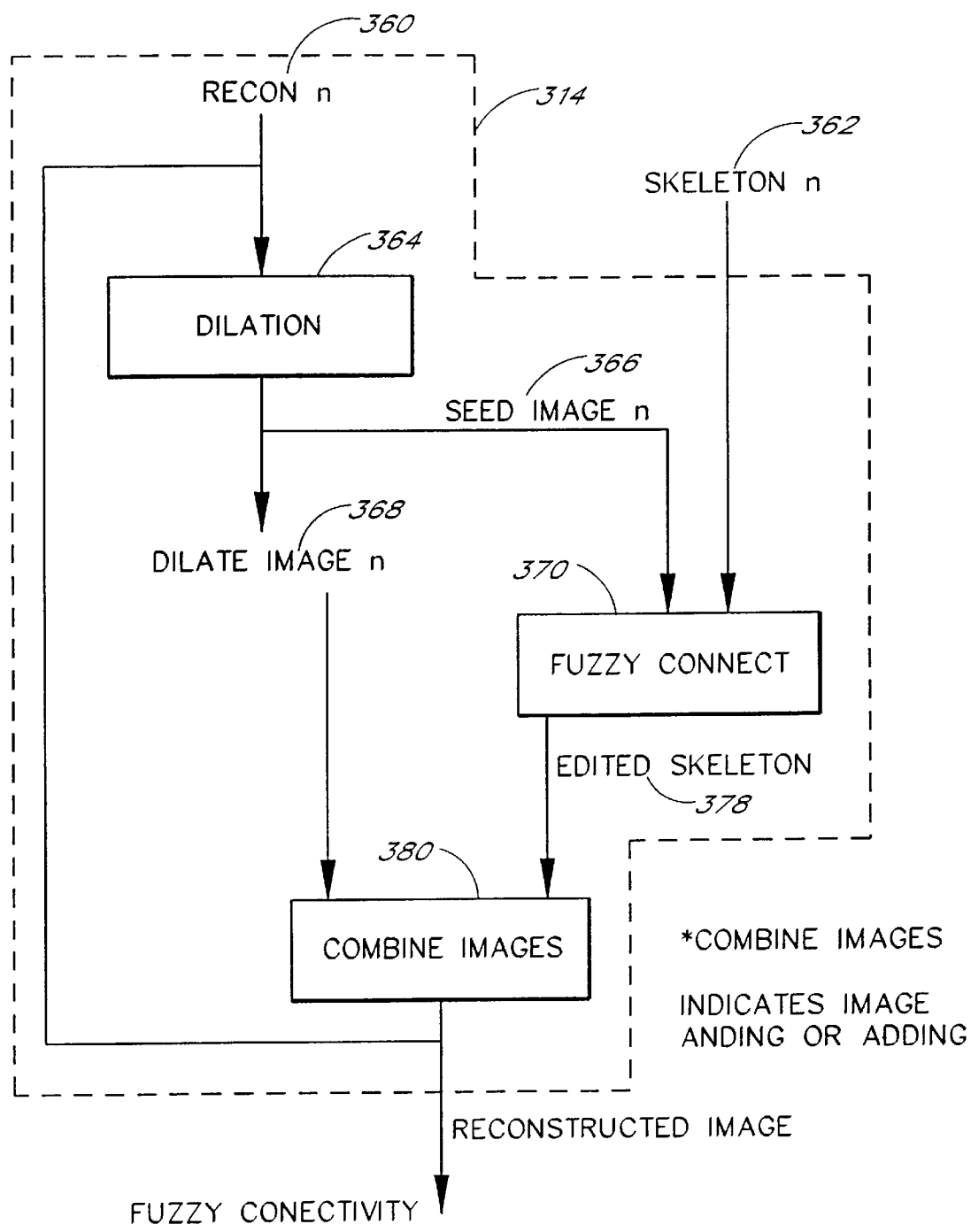
FIG. 23 is a block diagram of the morphological data decomposition and selective reconstruction process of a preferred embodiment of the present invention.

Referring to FIG. 23, the process of morphological data decomposition and selective reconstruction of the present invention is shown. Recon n 360 is subjected to dilation 364 so as to produce dilate image n 368 and seed image n 366. Seed image n is subjected to fuzzy connectivity criteria 370 with skeleton n 362 so as to produce edited skeleton 378. Dilate image n 368 is combined 380 with edited skeleton 378 to produce a new recon n 360 and the process is iterated.

The process of fuzzy connectivity already presented is valid for measuring the distance or difference between two sets. This distance, however, is primarily valid for measuring the distance between points in an image. A more specific measure of the distance of one image region from another is given with the following fuzzy region connectivity algorithm.

Figure 24:
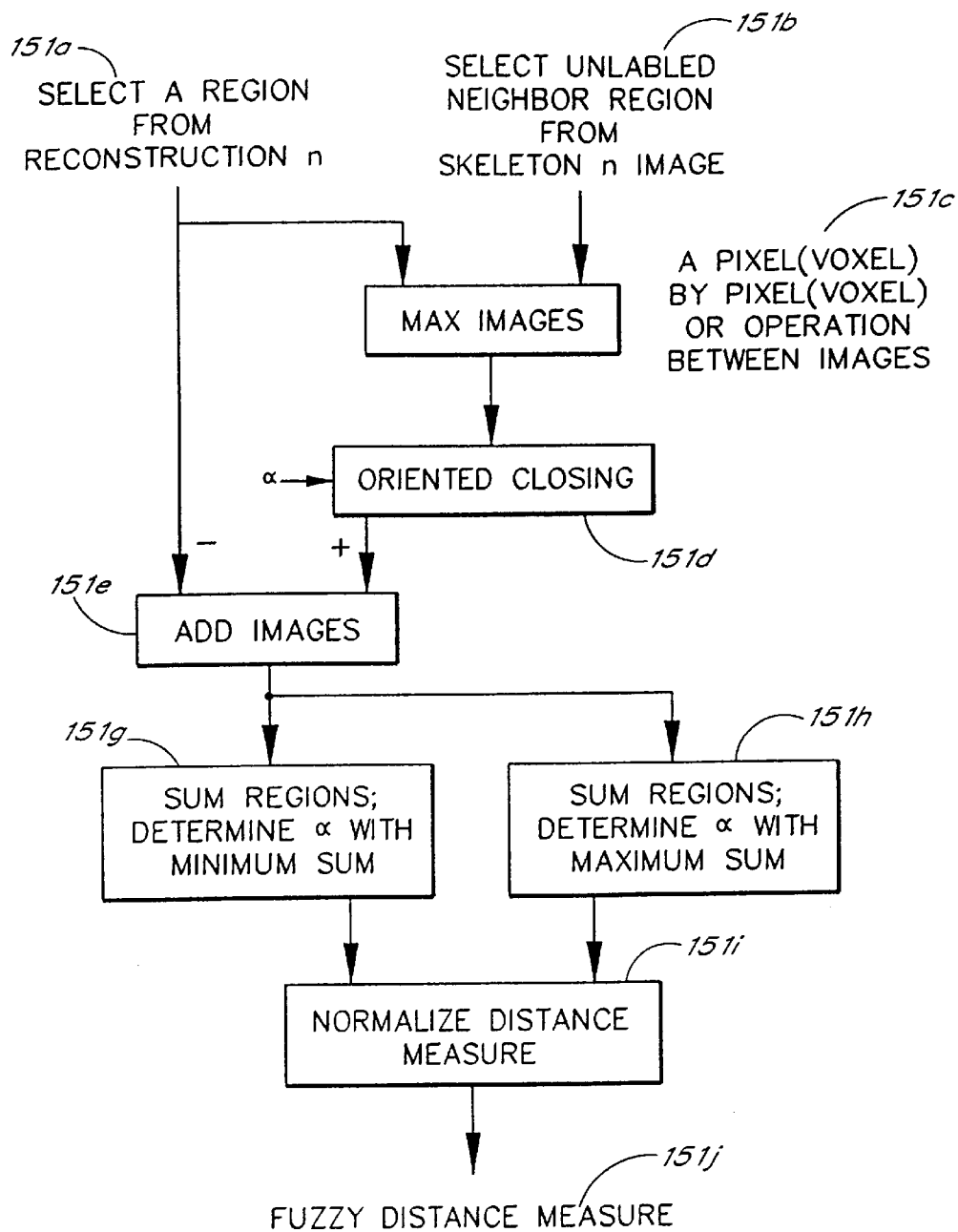
FIG. 24 is a block diagram of the fuzzy region connectivity method for measuring the distance of one image region from another.

As illustrated in FIG. 24, to determine a fuzzy distance, a region is elected from a reconstruction, reconstruction n 151a. A neighbor region is chosen from skeleton n image 151b. A pixel (voxel) by pixel (voxel) comparison is done between the two images, and the maximum value of each pixel is chosen 151c. After multiplying by an scaling factor, α, an oriented closing is done 151d and the negative of the original region from the reconstruction n 151a is added to the mentioned scaled result 151e. This procedure is repeated over an alpha range from zero to a maximum distance 151n, such as the diameter of the region of interest. The minimum distance measure over the range of α is the actual distance recorded 151g. This procedure is a more generalized method of obtaining the fuzzy distance from the Hausdorff distance metric given in equation 2.4.1. The procedure outlined in this paragraph results in the definition of a set of points covered by one of the two regions and excluding the set of points that is contained in both regions as shown by the shaded region in FIG. 25. To normalize the distance measure, the ratio of the α with a minimum sum to the a with a maximum sum is computed 151$i$.

Figure 26:
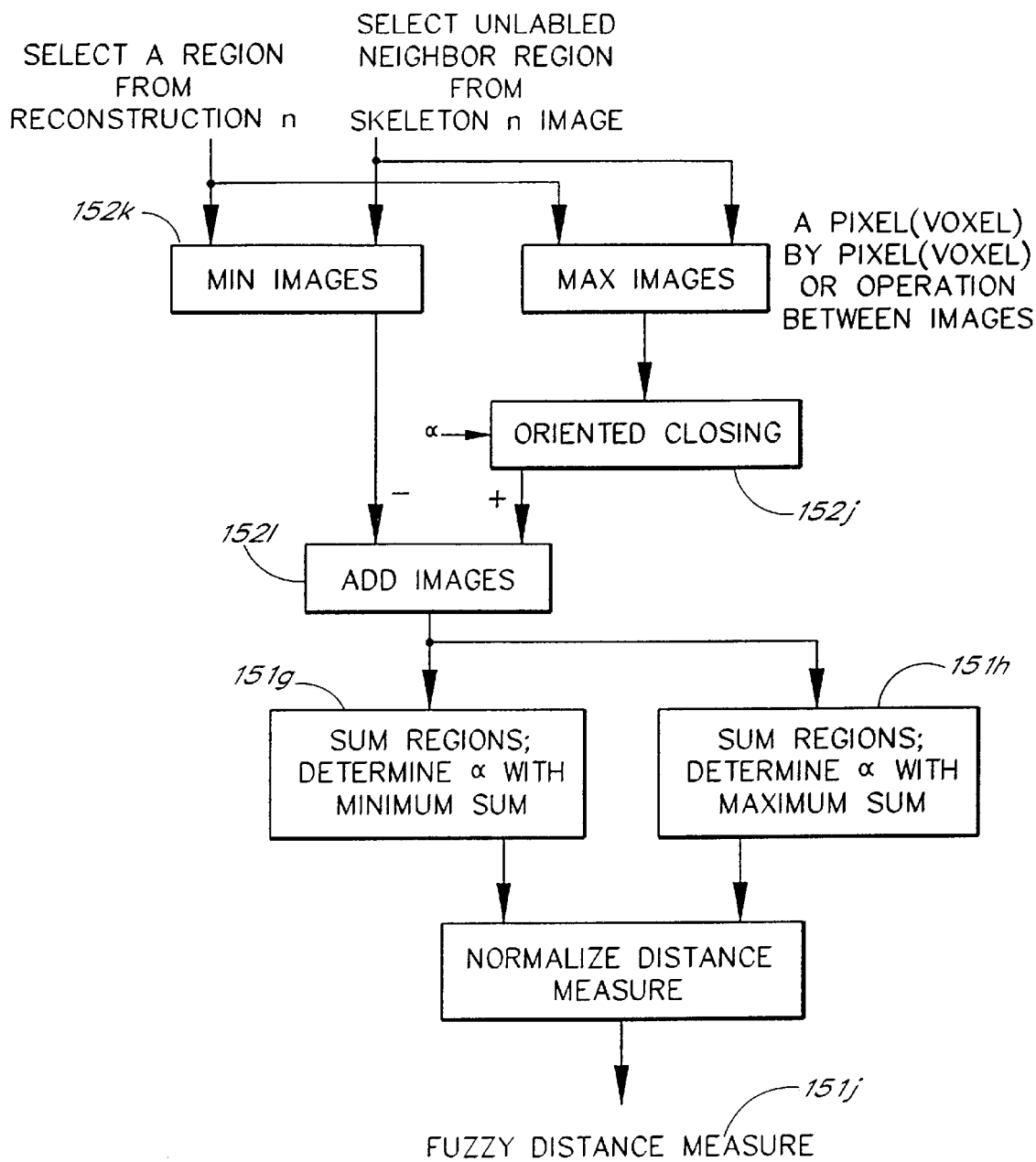
FIG. 26 is a block diagram of an alternative fuzzy region connectivity method for measuring the distance of one image region from another.

An alternative method is shown in FIG. 26. The method follows the same procedure as shown in FIG. 24 except that where a pixel by pixel comparison was done between the two images step 151$c$, not only the maximum value is maintained, but a minimum value is also retained 152$k$. In principle, fuzzy connectivity provides a means of measuring the spacial congruence of sets, however, the fuzzy operators of grayscale morphology are used to extend the measure of congruence between two sets or grayscale image distributions. After once again multiplying the maximum value by a scaling factor α and doing an oriented closing on the maximum value as shown in the block 152$j$, the negative of the minimum image is added to the resulting maximum image after the oriented closing and scaling 152$l$. This procedure repeated over an α range from zero to a maximum distance, such as the diameter of the region of interest. This procedure results in the defining of a set of points that is in either region but not in the intersection of the two regions as shown by the shaded region in FIG. 27.

The minimum distance over the range of α is the actual distance recorded. Regardless of which method is used, the method shown in FIG. 24 or the method shown in FIG. 26, the regions with α at a minimum are summed to form a single value 151$g$. The regions with α at a maximum are also summed to form a second single value 151$h$. Then the distance is normalized by dividing the alpha with a minimum sum by the alpha with a maximum sum giving a fuzzy distance measure 151$j$.

Figure 28:
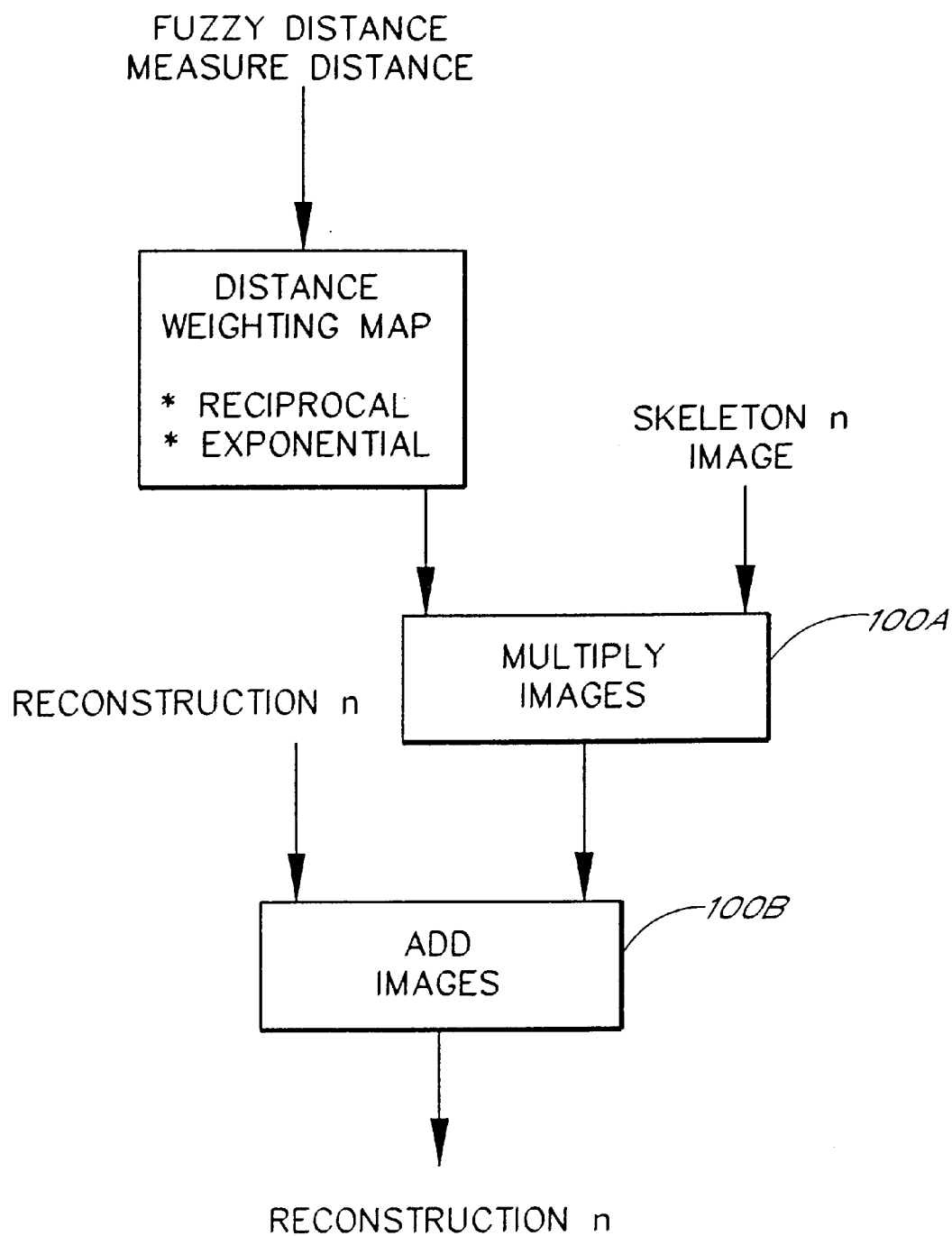
FIG. 28 is a block diagram of using the fuzzy distance to generate the fuzzy connectivity.

FIG. 28 shows the use of the fuzzy distance, d, to generate the fuzzy connectivity. The fuzzy connectivity or fuzzy measure may range from zero to one. The fuzzy connectivity can be directly mapped or determined as a function of the fuzzy distance. The fuzzy connectivity is determined by using one of three methods. It may be assigned as:

1) The reciprocal of the fuzzy distance or 1/d
2) The value given by exp(–d)
3) One minus the normalized value of d Once the fuzzy distance is determined, it can be used to weight the value of the appropriate set.

Figure 25:
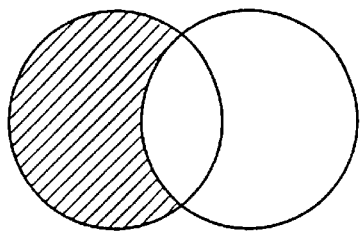
FIG. 25 defines a set which illustrates one measure of fuzzy distance.
Figure 27:
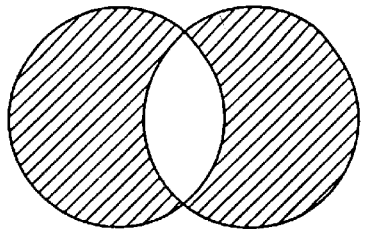
FIG. 27 defines a set which illustrates an alternative measure of fuzzy distance.

The fuzzy connectivity can represent one of two different sets. One interpretation is that the fuzzy connectivity is the set of all points that is included by one set or the other but not both sets as shown in FIG. 27. A second and preferred interpretation is that the fuzzy connectivity represents the set of all points included in one set but not included in the other set as shown in FIG. 25.

Referring to FIG. 28, the fuzzy connectivity can then be multiplied to the image from skeleton n as shown in 100A. The result is added to reconstruction n 100B to generate the new reconstruction n.

Figure 29:
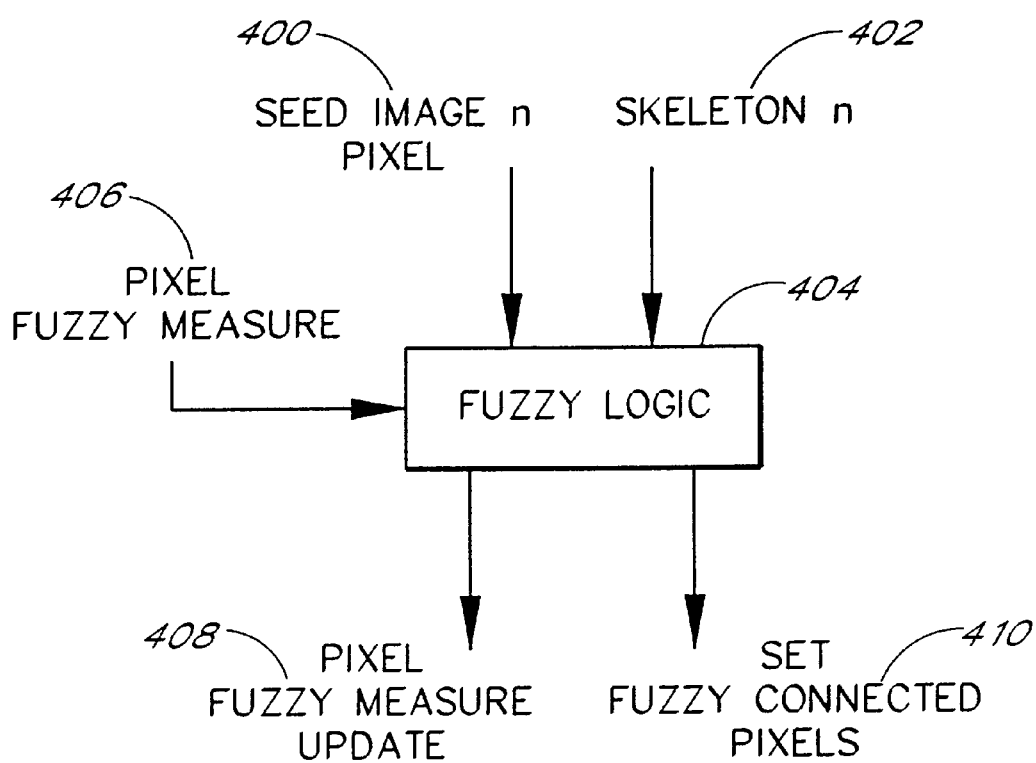
FIG. 29 is a block diagram of the fuzzy logic process of a preferred embodiment of the present invention.

Referring to FIG. 29, the use of fuzzy connectivity according to the present invention is shown. A seed image n pixel 400 and the skeleton n 402 are operated upon by fuzzy logic 404 utilizing pixel fuzzy logic measure 406, i.e., the selective structuring element, so as to provide pixel fuzzy measure update 408 and set fuzzy connected pixels 410.

The use of fuzzy logic in this manner is described in detail in "Analysis and Segmentation of Higher Dimensional Data Sets With Fuzzy Operators for Representation and Visualization" and published in *Neuro and Fuzzy Systems: Emergent Science of Intelligent Computing* by Mitra, Gupta, and Kraske, published by SPIE Press, 1994, ISBN 0-8194-1566-9, provided herewith and forming a part of this patent application, the entire contents of which are hereby incorporated by reference.

The above presented methods for mathematical morphological reconstruction offers a new capability for fusing and merging different data sets mapped over the same geometric region in space. In particular, size, shape and orientation features from different data set skeletons can be combined logically and with operations such as addition, subtraction, fuzzy connectivity, image maximization and minimization. One particularly useful example of this is shown in FIG. 30.

Figure 30:
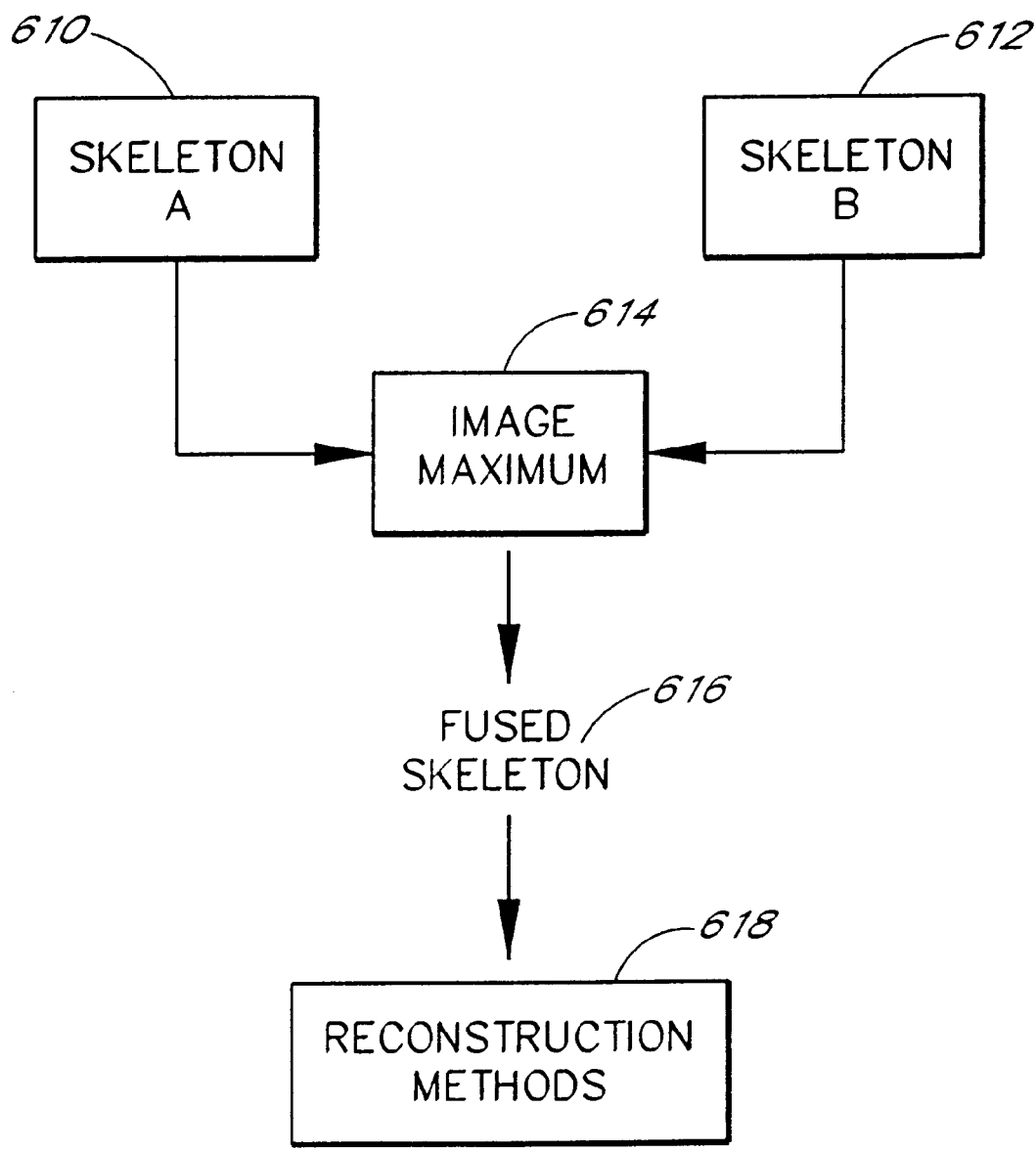
FIG. 30 is a flow diagram of one method of fusing data.

FIG. 30 demonstrates the use of fuzzy connectivity to merge two images. The first image, image A is skeletonized using standard skeletonization procedures to give skeleton A 610. The second image, image B is also skeletonized to give skeleton B 612. The two skeletons can be combined using a variety of methods. Those methods include assigning each pixel of the fused skeleton (resulting skeleton) 616 which is the sum of the corresponding pixels in skeleton A 610 and skeleton B 612. Alternately, the fused skeleton may receive the value of the smaller of the two corresponding pixels in a minimization function. However, the preferred embodiment, and the embodiment function implemented in the flowchart block 614 is the maximization function which assigns each pixel of the fused skeleton the larger of the values from the corresponding pixels in skeleton A and skeleton B. The resulting fused skeleton 616 can then be reconstructed using standard reconstruction methods 618 as discussed before.

After all the computation is completed, visualization of the voxels on a screen is necessary State of the art volumetric visualization techniques require mapping of data voxel volumes into various colors and transparencies. Morphological analysis and reconstruction techniques extend this to include size, shape, orientation and connectivity features.

There are two levels of incorporation of dimensional sieving fuzzy connectivity into volumetric visualization. First, the morphological classification of tissues, and second, the application of classical volumetric visualization algorithms which are commercially available off the shelf, such as those offered by AVS. The commercial algorithm enables one to replace the actual replacement of gradient and matrix normal computation functions with equivalent morphological algorithms, such as the replacement of a gradient with the subtraction of an append from a closed image or an eroded form from a dilated image surface.

It is understood that the exemplary methodology described herein and shown in the drawings represents only a presently preferred embodiment of the invention. As those skilled in the art will appreciate, the present invention is suitable for use in a variety of different applications, other than medical imaging. For example, the present invention may be utilized in geological searching. Entertainment applications include generating graphics for presentation. Aerospace applications also exist such as radar imaging, machine recognition, and various other imaging applications.

Indeed, various modifications and additions may be made to the described embodiment without departing from the spirit and scope of the invention. For example, various different shapes of structuring elements, other than those illustrated and described, may be utilized in either the morphological skeleton forming process or the reconstruction process. Additionally, various different criteria for defining the present membership of adjacent data points during reconstruction process are likewise suitable. Thus, these and other modifications and additions may be obvious to those skilled in the art and may be implemented to adapt to the present invention for use in a variety of different applications.

What is claimed is:

1. A method for isolating anatomical structures contained within a three-dimensional data set, the method comprising the steps of:

forming a morphological skeleton of the three-dimensional data set;

selecting a single seed data point consisting of a single voxel within the morphological skeleton, the seed data point being contained within a desired anatomical structure; and utilizing fuzzy connectivity to define additional data points of the desired anatomical structure to reconstruct substantially only the desired anatomical structure, wherein reconstruction of substantially only the desired anatomical structure facilitates viewing and analysis thereof.

2. The method as in claim 1, wherein the step of forming a morphological skeleton comprises recursive opening and erosion of the three-dimensional data set to form a plurality of residuals which define the morphological skeleton.

3. The method as in claim 1, wherein the step of forming a morphological skeleton comprises utilizing a generally spherical structuring element in recursive opening and erosion of the three-dimensional data set.

4. The method as in claim 1, wherein the step of selecting a seed data point comprises positioning a cursor at a desired point on an image displayed on a monitor.

5. The method as in claim 1, wherein the step of using fuzzy connectivity to define additional data points of the desired anatomical structure comprises defining connectivity based upon a size and shape of a structuring element utilizing a fuzzy generalization of mathematically defined distances between sets of data points as a criterion.

6. The method as in claim 1, wherein the step of reconstructing substantially only the desired anatomical structure comprises recursive dilation and closing of a selected portion of the morphological skeleton.

7. The method as in claim 1, wherein the step of utilizing fuzzy connectivity to define additional data points comprises defining connectivity based on the use of a generally spherical structuring element for defining distances between adjacent data points.

8. The method as in claim 1, wherein the three-dimensional data set comprises a data set generated by a device selected from a group consisting of:

a magnetic resonance imaging device;

a computer aid tomography device; and a positron emission tomography.

9. A method for reconstructing an anatomical structure from a morphological skeleton comprising:

selecting a single seed data point consisting of a single voxel within the morphological skeleton, the seed data point being contained within the desired anatomical structure; and utilizing fuzzy connectivity to define additional data points of the desired anatomical structure to reconstruct substantially only the desired anatomical structure, wherein the use of fuzzy connectivity results in reconstruction of substantially only the desired anatomical structure and substantially lacks surrounding tissue.

10. A method for fusing data from at least a first and a second medical image comprising the steps of:

reducing the second image to a size and scale corresponding to the first image;

converting the second image into a coordinate system corresponding to a predetermined coordinate utilized by a computer;

converting the first image into a coordinate system corresponding to the predetermined coordinate utilized by the computer;

using different resolutions and computer distance metrics to align the first image and the second image;

forming a first morphological skeleton of the first image;

forming a second morphological skeleton of the second image;

combining the first morphological skeleton with the second morphological skeleton into a fused skeleton;

selecting a single seed data point consisting of a single voxel within the fused skeleton, the seed data point being contained within a desired anatomical structure; and utilizing fuzzy connectivity to define additional data points to be combined and added to the desired anatomical structure.

11. The method for fusing data from at least a first and second medical image as in claim 10, wherein conversions of the second image into the predetermined coordinate system and conversion of the first image into the predetermined coordinate system is accomplished using a series of rotations and translations.

12. The method for fusing data from at least a first and second medical image as in claim 10, wherein the first morphological skeleton is combined with the second morphological skeleton by adding each pixel value in the first skeleton with a corresponding pixel value in the second skeleton, wherein the corresponding pixel in the fused skeleton is assigned a sum of the pixel values.

13. The method for fusing data from at least a first and second medical image as in claim 10, wherein the first morphological skeleton is combined with the second morphological skeleton by comparing each pixel value in the first skeleton with a corresponding pixel value in the second skeleton, wherein the corresponding pixel in the fused skeleton is assigned a value of the larger value of the pixel in the first skeleton and the pixel in the second skeleton.

14. The method for fusing data from at least a first and second medical image as in claim 10, wherein the first morphological skeleton is combined with the second morphological skeleton by comparing each pixel value in the first skeleton with a corresponding pixel value in the second skeleton, wherein the corresponding pixel in the fused skeleton is assigned a value of the smaller value of the pixel in the first skeleton and the pixel in the second skeleton.

15. The method for fusing data from at least a first and second medical image as in claim 10, wherein a fuzzy correction is conducted on the data points before fuzzy reconstruction is performed.

* * * * *

(12) EX PARTE REEXAMINATION CERTIFICATE (10718th)
United States Patent
George, III et al.

(10) Number: US 6,175,655 C1
(45) Certificate Issued: Sep. 23, 2015

(54) MEDICAL IMAGING SYSTEM FOR DISPLAYING, MANIPULATING AND ANALYZING THREE-DIMENSIONAL IMAGES

(75) Inventors: Frederick W. George, III, San Marino, CA (US); Wolfgang F. Kraske, Pasadena, CA (US)

(73) Assignee: 3D MEDICAL IMAGING SYSTEMS, LLC., Braselton, GA (US)

Reexamination Request:
No. 90/013,419, Dec. 30, 2014

Reexamination Certificate for:
Patent No.: 6,175,655
Issued: Jan. 16, 2001
Appl. No.: 08/715,920
Filed: Sep. 19, 1996

Related U.S. Application Data

(60) Provisional application No. 60/004,126, filed on Sep. 20, 1995.

(51) Int. Cl.
*G06F 19/00* (2011.01)

(52) U.S. Cl.
CPC .......... *G06F 19/3437* (2013.01); *G06F 19/321* (2013.01)

(58) Field of Classification Search
None
See application file for complete search history.

(56) References Cited

To view the complete listing of prior art documents cited during the proceeding for Reexamination Control Number 90/013,419, please refer to the USPTO's public Patent Application Information Retrieval (PAIR) system under the Display References tab.

*Primary Examiner* — Behzad Peikari

(57) ABSTRACT

A method and device for generating, displaying and manipulating three-dimensional images for medical applications is provided. The method creates a three-dimensional images from MRI or other similar medical imaging equipment. The medical imaging system allows a user to view the three-dimensional model at arbitrary angles, vary the light or color of different elements, and to remove confusing elements or to select particular organs for close viewing. Selection or removal of organs is accomplished using fuzzy connectivity methods to select the organ based on morphological parameters.

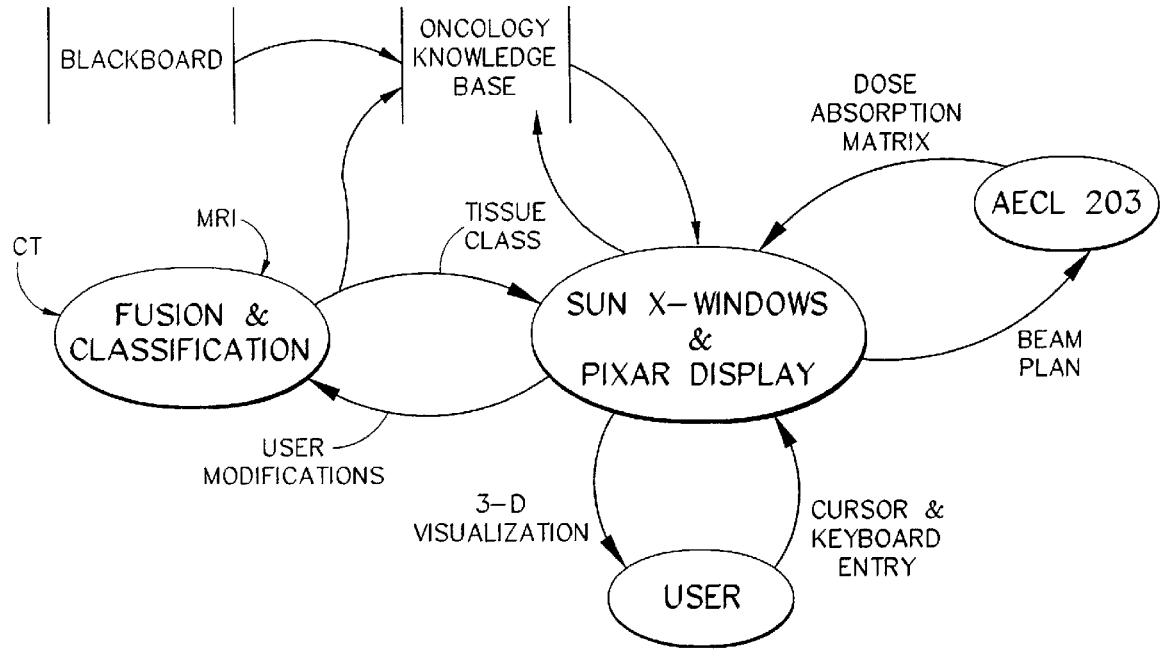

EX PARTE REEXAMINATION CERTIFICATE

NO AMENDMENTS HAVE BEEN MADE TO THE PATENT

AS A RESULT OF REEXAMINATION, IT HAS BEEN DETERMINED THAT:

The patentability of claims 1-15 is confirmed.

\* \* \* \* \*